US011660365B2

(12) United States Patent
Thompson et al.

(10) Patent No.: US 11,660,365 B2
(45) Date of Patent: May 30, 2023

(54) APPARATUS AND METHOD FOR STERILIZING MEDICAL DEVICES

(71) Applicant: ASP Global Manufacturing GmbH, Schaffhausen (CH)

(72) Inventors: Brian J. Thompson, Aliso Viejo, CA (US); Jacob S. Childs, Huntingdon Beach, CA (US); Chunhui Xie, Hebei (CN); Marco A. Mangiaterra, La Habra, CA (US); Darius D. Eghbal, Sierra Madre, CA (US); Margaret D. Shaffer, San Clemente, CA (US); Jeremy M. Yarwood, Aliso Viejo, CA (US); Benjamin M. Fryer, Lake Forest, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 410 days.

(21) Appl. No.: 16/868,683

(22) Filed: May 7, 2020

(65) Prior Publication Data
US 2020/0330636 A1    Oct. 22, 2020

Related U.S. Application Data

(62) Division of application No. 15/441,707, filed on Feb. 24, 2017, now Pat. No. 10,668,180.

(Continued)

(51) Int. Cl.
*A61L 2/28* (2006.01)
*A61L 2/24* (2006.01)
*A61B 1/12* (2006.01)

(52) U.S. Cl.
CPC .............. *A61L 2/28* (2013.01); *A61B 1/123* (2013.01); *A61L 2/24* (2013.01); *A61L 2202/14* (2013.01); *A61L 2202/24* (2013.01)

(58) Field of Classification Search
CPC .............. A61L 2/24; A61L 2/28; A61B 1/123
See application file for complete search history.

(56) References Cited

U.S. PATENT DOCUMENTS

| 4,744,951 A | * | 5/1988 | Cummings | ............ A01N 59/00 422/27 |
| 5,863,790 A | | 1/1999 | Bolea | |

(Continued)

FOREIGN PATENT DOCUMENTS

| CN | 1492769 A | 4/2004 |
| CN | 1663618 A | 9/2005 |

(Continued)

OTHER PUBLICATIONS

Tanaka, K., et al., "Evaluation of Perioperative Management Using Information Communication Technology—Construction of a Management System for Sterilization of Medical Instruments, Reservations System for Surgery, and Operation Workflow Management System—," Journal of the Japanese Society of Environmental Infections, 2008, 23(2):104-110, 10 pgs.

(Continued)

Primary Examiner — Kevin Joyner
(74) Attorney, Agent, or Firm — Frost Brown Todd LLP

(57) ABSTRACT

A sterilizing cabinet performs a method of processing a medical device, such as a used medical device or an otherwise non-sterile medical device. The method includes receiving input from a user selecting a sterilization cycle from a plurality of available sterilization cycles. The sterilizing cabinet identifies a biological indicator associated with the selected sterilization cycle. The sterilizing cabinet prompts the user via a touch screen display to place the medical device and the biological indicator into a sterilization chamber of a sterilizing cabinet. The sterilizing cabinet performs load conditioning on the medical device in the sterilization chamber. The sterilizing cabinet then performs (Continued)

the selected sterilization cycle on the medical device in the sterilization chamber after completing the act of load conditioning.

20 Claims, 15 Drawing Sheets

Related U.S. Application Data

(60) Provisional application No. 62/376,517, filed on Aug. 18, 2016, provisional application No. 62/316,722, filed on Apr. 1, 2016, provisional application No. 62/302,257, filed on Mar. 2, 2016.

(56) References Cited

U.S. PATENT DOCUMENTS

| | | | |
|---|---|---|---|
| 5,955,296 | A | 9/1999 | Roll |
| 6,063,591 | A | 5/2000 | Bolea |
| 6,251,345 | B1 * | 6/2001 | Palmers ............... A61B 90/70 422/295 |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,485,978 | B1 | 11/2002 | Kirckof et al. |
| 6,852,277 | B2 | 2/2005 | Platt et al. |
| 6,852,279 | B2 | 2/2005 | Williams et al. |
| 6,936,434 | B2 | 8/2005 | McDonnell et al. |
| 6,939,519 | B2 | 9/2005 | Agamohamadi et al. |
| 6,986,736 | B2 | 1/2006 | Williams et al. |
| 7,138,087 | B1 | 11/2006 | Malkin et al. |
| 7,479,257 | B2 | 1/2009 | Nguyen et al. |
| 7,686,761 | B2 | 3/2010 | Jackson et al. |
| 7,899,681 | B2 | 3/2011 | Katzenmaier et al. |
| 8,246,909 | B2 | 8/2012 | Williams et al. |
| 9,056,147 | B2 | 6/2015 | Ma |
| 9,068,976 | B2 | 6/2015 | Putnam et al. |
| 9,216,440 | B2 | 12/2015 | Ma et al. |
| 9,410,180 | B2 | 8/2016 | Pederson et al. |
| 10,201,269 | B2 | 2/2019 | Yang et al. |
| 10,443,083 | B2 | 10/2019 | Eghbal et al. |
| 10,561,753 | B2 | 2/2020 | Thompson et al. |
| 10,596,287 | B2 | 3/2020 | Dang et al. |
| 10,668,180 | B2 | 6/2020 | Thompson et al. |
| 2002/0009015 | A1 | 1/2002 | Laugharn et al. |
| 2003/0083902 | A1 | 5/2003 | Hehenberger et al. |
| 2003/0170901 | A1 | 9/2003 | Kippenhan et al. |
| 2004/0197848 | A1 | 10/2004 | Behun et al. |
| 2013/0217107 | A1 | 8/2013 | Pederson et al. |
| 2013/0323117 | A1 | 12/2013 | Ma et al. |
| 2013/0323120 | A1 | 12/2013 | Ma |
| 2014/0053871 | A1 | 2/2014 | Ma et al. |
| 2014/0235975 | A1 | 8/2014 | Carnes |
| 2014/0264039 | A1 | 9/2014 | Kurkowski et al. |
| 2015/0314021 | A1 * | 11/2015 | Botos .................. A61L 2/025 422/128 |
| 2017/0252472 | A1 | 9/2017 | Dang et al. |
| 2017/0252473 | A1 | 9/2017 | Thompson et al. |
| 2017/0252474 | A1 | 9/2017 | Thompson et al. |
| 2017/0253845 | A1 | 9/2017 | Amin |
| 2017/0253905 | A1 | 9/2017 | Eghbal et al. |
| 2020/0063179 | A1 | 2/2020 | Eghbal et al. |
| 2020/0179549 | A1 | 6/2020 | Thompson et al. |

FOREIGN PATENT DOCUMENTS

| | | |
|---|---|---|
| CN | 101095961 A | 1/2008 |
| CN | 101189519 A | 5/2008 |
| CN | 102245217 A | 11/2011 |
| CN | 102256631 A | 11/2011 |
| CN | 102364485 A | 2/2012 |
| CN | 102498218 A | 6/2012 |
| CN | 102740898 A | 10/2012 |
| CN | 103119173 A | 5/2013 |
| CN | 103201391 A | 7/2013 |
| CN | 103559572 A | 2/2014 |
| CN | 103606118 A | 2/2014 |
| CN | 104056292 A | 9/2014 |
| CN | 104380333 A | 2/2015 |
| CN | 104567982 A | 4/2015 |
| CN | 204671599 U | 9/2015 |
| CN | 105120906 A | 12/2015 |
| EP | 0629410 A1 | 12/1994 |
| EP | 1617878 A1 | 1/2006 |
| EP | 0981641 B1 | 5/2006 |
| EP | 2340853 A1 | 7/2011 |
| EP | 2792294 A1 | 10/2014 |
| JP | 2000-175995 A | 6/2000 |
| JP | 2008-200126 A | 9/2008 |
| JP | 2009-095502 A | 5/2009 |
| JP | 2009-532090 A | 9/2009 |
| JP | 2010-119491 A | 6/2010 |
| JP | 2012-071029 A | 4/2012 |
| JP | 2012-105713 A | 6/2012 |
| JP | 2014-166209 A | 9/2014 |
| JP | 2014-179973 A | 9/2014 |
| KR | 2018-0038868 A | 4/2018 |
| RU | 2302000 C2 | 7/2007 |
| RU | 2522203 C2 | 7/2014 |
| WO | WO 96/25214 A1 | 8/1996 |
| WO | WO 2001/010475 A1 | 2/2001 |
| WO | WO 2004/093925 A1 | 11/2004 |
| WO | WO 2005/048041 A2 | 5/2005 |
| WO | WO 2006/086547 A2 | 8/2006 |
| WO | WO 2013/181393 A1 | 12/2013 |
| WO | WO 2014/159696 A1 | 10/2014 |
| WO | WO 2015/049002 A1 | 4/2015 |
| WO | WO 2015/080777 A1 | 6/2015 |

OTHER PUBLICATIONS

Noboru, K., "Sterilization indicator," Japanese Journal of Operating Room Nursing, Special Edition "The basics of sterilization that you should know now," Mar. 2003, (Sequential serial No. 227), 18(3):274-280. (Article not available, Bibliographic material attached. Please consider as prior art until proven otherwise.) 1 pg.
Chinese Search Report dated Jun. 11, 2021 for Application No. CN 201710120894.1, 1 pg.
Japanese Office Action, Notice of Reasons for Refusal, and First Search, dated Dec. 8, 2020 for Application No. JP 2017-038014, 18 pgs.
Japanese Search Report dated Oct. 23, 2020 for Application No. JP2017-038026, 32 pgs.
Japanese Office Action, Notice of Reasons for Refusal, dated Apr. 27, 2021 for Application No. JP 2017-038032, 5 pgs.
Chinese Office Action dated Dec. 25, 2020, for Application No. 201710120893.7, 17 pages.
Japanese Notification of Reasons for Refusal dated Dec. 8, 2020 for Application No. 2017-038026, 4 pages.
Russian Office Action and Search Report dated Jun. 27, 2018 for Application No. 2017106748, 10 pages.
Chinese Office Action and Search Report dated Jan. 5, 2021 for Application No. 201710120894.1, 10 pages.
Chinese Office Action and Search report dated Apr. 14, 2020 for Application No. 201710120892.2, 13 pages.
Chinese Office Action and Search report dated May 7, 2020 for Application No. 201710120893.7, 16 pages.
European Search Report and Written Opinion, Extended, dated Jul. 27, 2017 for Application No. EP 17158975.7, 9 pages.
European Search Report and Written Opinion, Partial, dated Aug. 1, 2017 for Application No. EP 17158813.0, 13 pages.
Extended European Search Report and Written Opinion dated Aug. 2, 2017 for Application No. EP 17158962.5, 8 pages.
European Search Report and Written Opinion, Extended, dated Nov. 9, 2017 for Application No. EP 17158813.0, 11 pages.
U.S. Appl. No. 62/302,257, filed Mar. 2, 2016.
U.S. Appl. No. 62/316,722, filed Apr. 1, 2016.
U.S. Appl. No. 62/376,517, filed Aug. 18, 2016.

(56) References Cited

OTHER PUBLICATIONS

Chinese Final Office Action dated Jan. 22, 2021, for Application No. 201710120892.2, 9 pages.
Chinese Office Action, The Second Office Action, dated Sep. 30, 2020 for Application No. CN 201710120892.2, 12 pgs.
Chinese Office Action, The First Office Action, and First Search Report dated Jul. 31, 2020 for Application No. CN 201710120894.1, 20 pgs.
European Examination Report dated Sep. 16, 2020 for Application No. EP 17158962.5, 4 pgs.
European Examination Report dated Sep. 16, 2020 for Application No. EP 17158975.7, 4 pgs.
Japanese Search Report dated Jul. 27, 2020 for Application No. JP 2017-038032, 159 pgs.

* cited by examiner

APPARATUS AND METHOD FOR STERILIZING MEDICAL DEVICES

PRIORITY

This application is a divisional of U.S. patent application Ser. No. 15/441,707, entitled "Apparatus and Method for Sterilizing Medical Devices," filed Feb. 24, 2017, and issued as U.S. Pat. No. 10,668,180 on Jun. 2, 2020.

This application claims priority to U.S. Provisional Patent Application No. 62/302,257, entitled "System and Method for Sterilizing Medical Devices," filed Mar. 2, 2016, the disclosure of which is incorporated by reference herein.

This application also claims priority to U.S. Provisional Patent Application No. 62/316,722, entitled "System and Method for Sterilizing Medical Devices," filed Apr. 1, 2016, the disclosure of which is incorporated by reference herein.

This application also claims priority to U.S. Provisional Patent Application No. 62/376,517, entitled "Apparatus and Method to Link Medical Device Sterilization Equipment," filed Aug. 18, 2016, the disclosure of which is incorporated by reference herein.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, and vapor phase sterilization, either with or without a gas plasma and ethylene oxide (EtO). Each of these methods may depend to a certain extent on the diffusion rates of the sterilization fluids (e.g., gases) upon the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging may help prevent contamination of a sterile medical device, the packaging may increase the difficulty of achieving a successful sterilization cycle because the packaging may impede the sterilant from reaching the medical device contained therein. This may be particularly problematic for medical devices that have diffusion-restricted spaces therein because these diffusion-restricted spaces may reduce the likelihood that a sterilization cycle may be effective. For example, some endoscopes have a long narrow lumen into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; and U.S. Pat. No. 6,447,719, entitled "Power System for Sterilization Systems Employing Low Frequency Plasma," issued Sep. 10, 2002, the disclosure of which is incorporated by reference herein. Medical devices must be carefully arranged and controlled within the sterilization system to maintain an environment that allows for effective sterilization. Each different medical device may require a different arrangement and sterilization process, meaning that use of a sterilization system can still be error prone and may heavily rely upon operator training and knowledge, or related documentation.

In addition, re-use of the same sterilizing chamber of a sterilization system may result in cross contamination, particularly when the sterilization system is not operated correctly. Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle.

In view of the foregoing, it may be desirable to provide a sterilization system that minimizes opportunities for operator error, thereby maximizing the likelihood of successful sterilization cycles, thereby minimizing the risk of patient infection. While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Sterilization System and Devices

Figure 1:
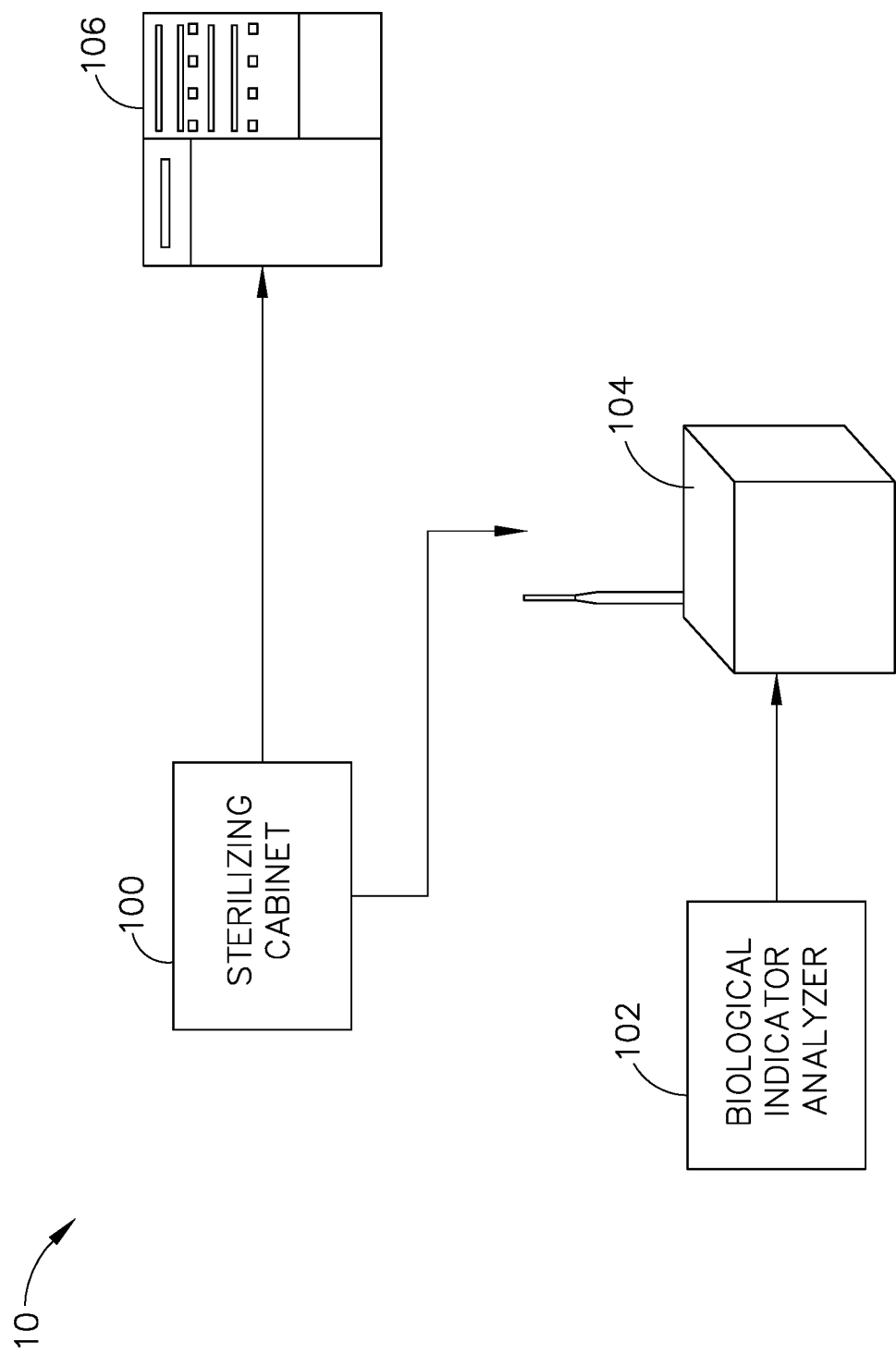
FIG. 1 depicts a schematic view of an exemplary sterilization system.

FIG. 1 depicts a schematic view of an exemplary system (10) of interconnected devices that may be configured to perform methods for sterilizing medical devices. System (10) of this example includes a sterilizing cabinet (100), a biological indicator analyzer (102), a communication hub (104), and a server (106). As will be described in greater detail below, sterilizing cabinet (100) may have a sealable sterilization chamber where contaminated medical devices may be placed. A user may interact with sterilizing cabinet (100) via a set of user inputs, such as physical buttons, a keyboard, a touch pad or mouse, other controls, and/or a touch screen display interface. A display of sterilizing cabinet (100) may provide users with information, configuration options, status and duration of sterilization cycles and preparation, and other similar information.

Sterilizing cabinet (100) is in communication with a server (106), such as a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also provide information to the sterilizing cabinet (100) such as software updates, configuration updates, user authentication information, biological indicator use protocols, and other information. Communication between sterilizing cabinet (100) and server (106) may be accomplished via any suitable wired and/or wireless communication technology, such as Ethernet, Wi-Fi, Bluetooth, USB, infrared, NFC, and/or other technologies.

In system (10) of the present example, sterilizing cabinet (100) is also in communication with a communication hub (104), which itself is in communication with one or more biological indicator analyzers (102). As will be described in greater detail below, biological indicator analyzer (102) may comprise a desktop or wall mounted device that receives a biological indicator and measures one or more characteristics of the biological indicator in order to gather data that may be used to determine whether the biological indicator tests positive, indicating that contamination is present after a sterilization procedure; or negative, indicating that no contamination is present after the sterilization procedure.

In some versions, biological indicator analyzer (102) will measure and transmit data to communication hub (104), which will process the data to determine if there is contamination. In other versions, biological indicator analyzer (102) itself may both measure and analyze the data to determine whether there is contamination, and communication hub (104) may be used to receive, gather, and transmit such information to sterilizing cabinet (100) and/or other devices as will be described in greater detail below. In still other versions, biological indicator analyzer (102) and communication hub (104) may be different components of a single device; or may be components of sterilizing cabinet (100). Such variations may be desirable depending upon a particular implementation environment and user needs, such that a single device incorporating sterilizing cabinet (100), communication hub (104), and biological indicator analyzer (102) may be desirable in a semi-portable unit; while an implementation supporting a one-to-many relationship between sterilizing cabinet (100) and biological indicator analyzer (102) may be more advantageous for permanent installation in a large hospital with many users.

As will be described in greater detail below and as alluded to above, communication hub (104) is configured to process and relay information from biological indicator analyzer (102) to sterilizing cabinet (100). Biological indicator analyzer (102) and sterilizing cabinet (100) may each be coupled with communication hub (104) via any suitable wired and/or wireless communication technology, such as Ethernet, Wi-Fi, Bluetooth, USB, infrared, NFC, and/or other technologies. It should also be understood that communication hub (104) may be in communication with various other components, via wire or wirelessly, including but not limited to desktop computers, laptop computers, mobile computing devices, smartphones, etc. Moreover, communication hub (104) may be in communication with server (106) via wire or wirelessly. In versions where communication hub (104) is in communication with server (106), communication hub (104) may relay data, etc., between sterilizing cabinet (100) and server (106), such that communication hub (104) serves as an intermediary between sterilizing cabinet (100) and server (106). It should therefore be understood that, in some versions, sterilizing cabinet (100) may be in communication with server (106) via communication hub (104) instead of being directly in communication with server (106). By way of example only, communication hub (104) may be constructed and operable in accordance with at least some of the teachings of U.S. Provisional Patent Application No. 62/376,517, entitled "Apparatus and Method to Link Medical Device Sterilization Equipment," filed Aug. 18, 2016, the disclosure of which is incorporated by reference herein. Various other suitable components and configurations that may be used to form communication hub (104) will be apparent to those of ordinary skill in the art in view of the teachings herein.

II. Exemplary Sterilization Processes and Interfaces

A. Overview of Sterilization Process

Figure 2:
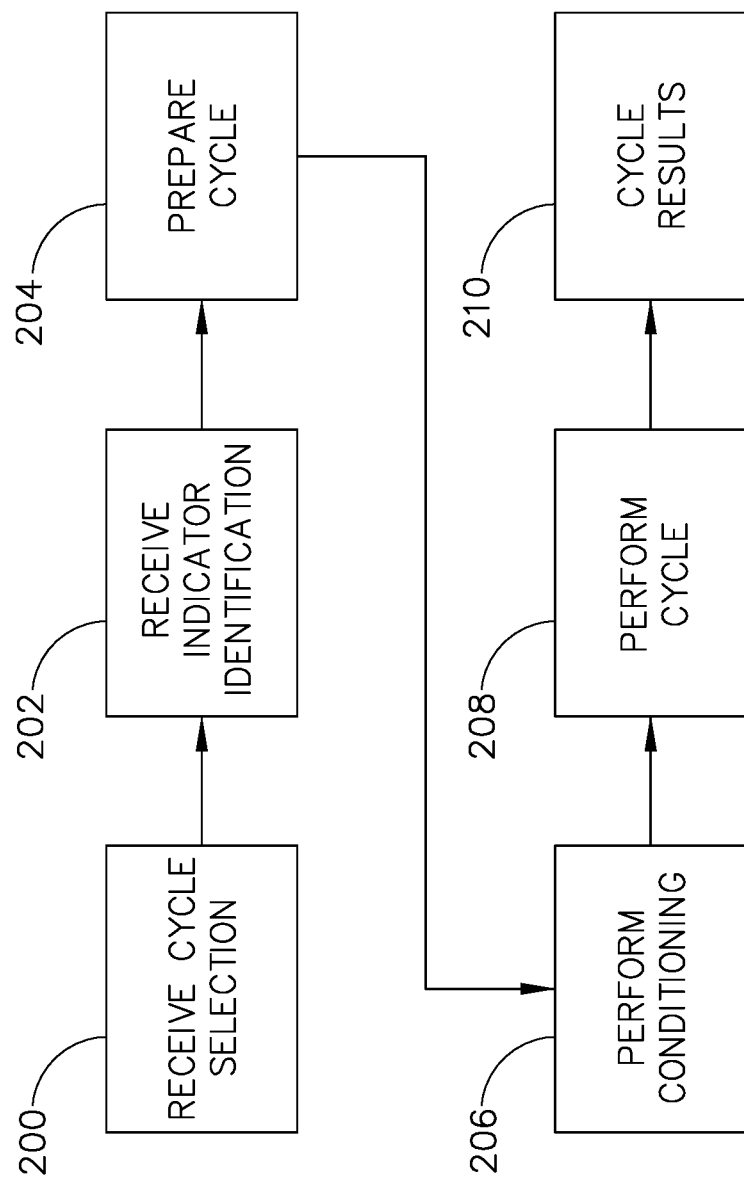
FIG. 2 depicts a high level flowchart of an exemplary set of steps that a sterilizing cabinet of the system of FIG. 1 could perform to sterilize a medical device.

FIG. 2 depicts a high level flowchart of an exemplary set of steps that system (10) could perform to sterilize a medical device. A user may interact with the system via a user interface such as a keyboard or touch screen of sterilizing cabinet (100), as will be described in greater detail below; or via an input device in communication with sterilizing cabinet (100). Initially, sterilizing cabinet (100) may display one or more sterilization cycles via a display and then receive a sterilization cycle selection (block 200) from the user. Sterilizing cabinet (100) may be configured to perform one or more sterilization cycles, with different sterilization cycles being appropriate for different types and quantities of medical devices.

Sterilizing cabinet (100) may also display instructions indicating whether a biological indicator should be used with the selected sterilization cycle, and receive a biological indicator identification (block 202). A biological indicator may be placed inside a sterilization chamber of sterilizing cabinet (100) before the sterilization cycle begins and may remain in the sterilization chamber during a sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations. When used, a biological indicator may be identified by manual input, such as keyboard entry of a biological indicator type or identifier; or may be identified automatically, such as by an optical scan of an optical identifier or a wireless scan of an RFID or other unique identifier.

Selection of a sterilization cycle (block 200) and identification of a biological indicator (block 202) may define one or more requirements for the configuration and arrangement of medical devices within sterilizing cabinet (100). A door of the sterilization chamber of sterilizing cabinet (100) may be opened and instructions may be displayed to guide a user through preparation of the sterilization cycle (block 204), including placement of the biological indicator, placement of medical devices, closing the door of the sterilization chamber of the sterilization cabinet (100), and/or other changes in preparation.

Before initiating the actual sterilization cycle (block 208), sterilization cabinet (100) may also perform load conditioning (block 206) of the medical devices that are loaded in the sterilization chamber of the sterilization cabinet (100). Such load conditioning (block 206) may include verifying that the sterilization chamber is sealed; verifying contents of the sterilization chamber; checking physical characteristics of the contents of the sterilization chamber such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in the sterilization chamber for the sterilization cycle.

Once the load conditioning (block 206) has been completed, the selected sterilization cycle itself may be performed (block 208). The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. After the sterilization cycle (block 208) is completed, the complete sterilization results may be displayed to a user via a display of the sterilization cabinet; transmitted to server (106);

printed locally; and/or displayed, transmitted, and/or stored via other devices as may be desirable.

Sterilization cabinet (100) may also provide results (block 210) of the sterilization cycle. This provision of results (block 210) may include results from analysis of a biological indicator via biological indicator analyzer (102) as described below. These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history in order to determine if other past cycles may be the cause of the contamination; and/or if subsequently sterilized medical devices may need to be re-sterilized.

Figure 3:
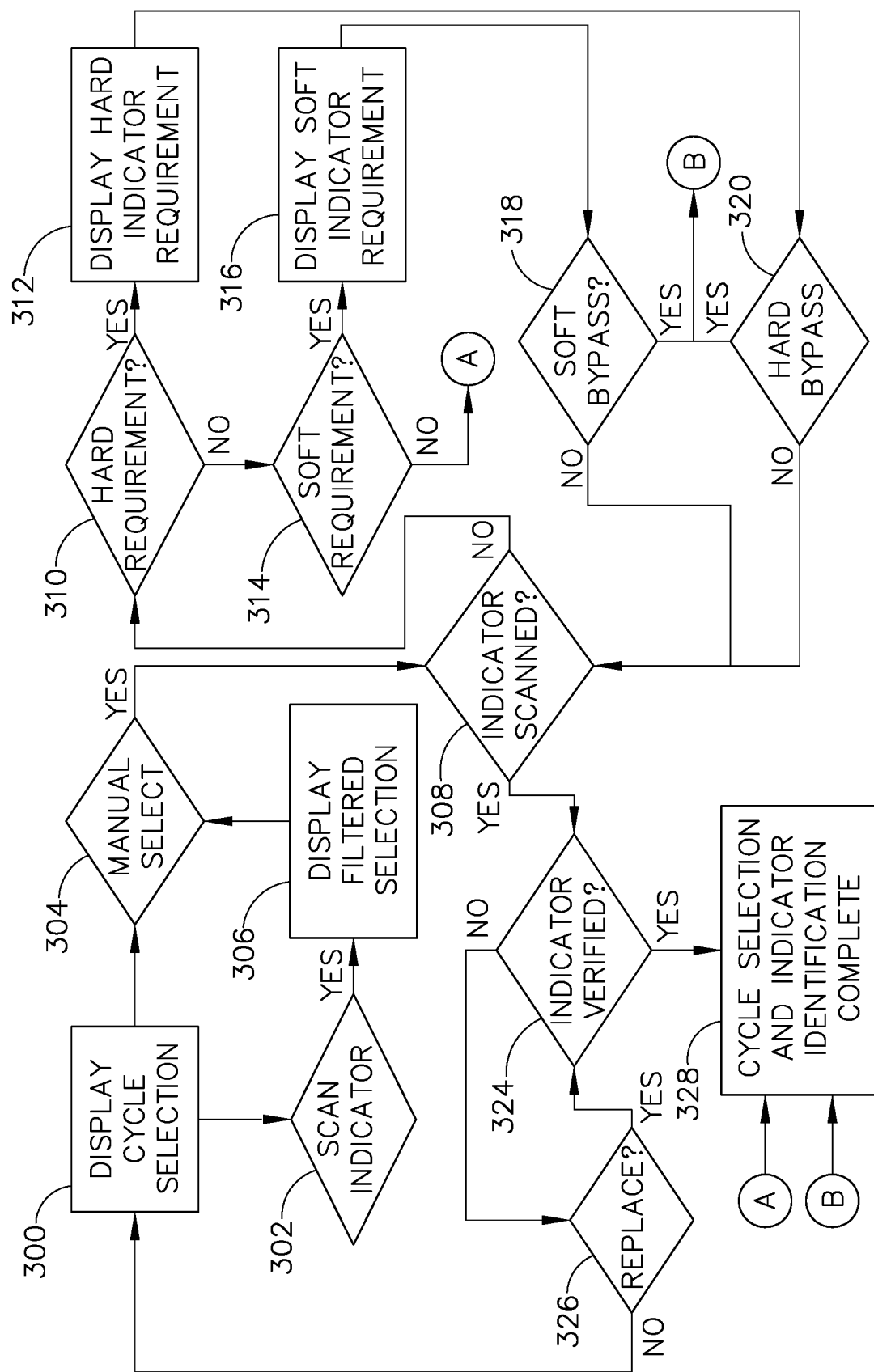
FIG. 3 depicts a flowchart of an exemplary set of steps that the sterilizing cabinet of the system of FIG. 1 could perform to determine a sterilization cycle and associated configuration.

B. Exemplary Sterilization Cycle Selection and Biological Indicator Identification FIG. 3 shows an exemplary set of steps that sterilizing cabinet (100) could perform to receive a sterilization cycle selection (block 200) and receive a biological indicator identification (block 202). In other words, the method shown in FIG. 3 may be viewed as showing several sub-steps that may be performed as part of the sterilization cycle selection step (block 200) and the biological indicator identification step (block 202) of FIG. 2.

Figure 6:
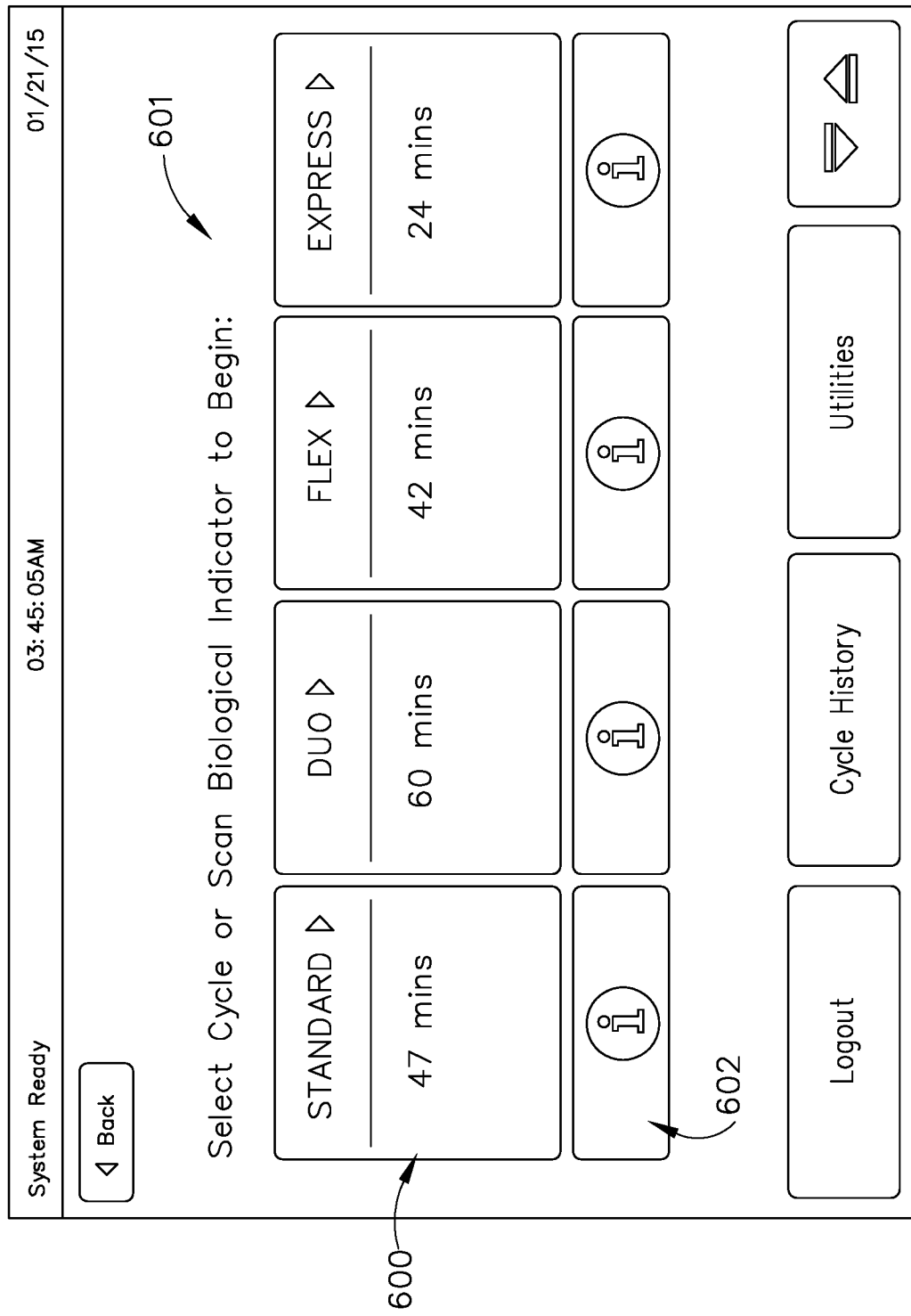
FIG. 6 depicts a screenshot of an exemplary user interface that could be presented via the sterilizing cabinet of the system of FIG. 1, to select a sterilization cycle.

When a user initially interacts with sterilizing cabinet (100), after logging in or otherwise authenticating their use of the sterilizing cabinet (100), sterilizing cabinet (100) may display a sterilization cycle selection (block 300) to the user via a graphical user interface such as the one shown in FIG. 6. As shown in FIG. 6, a sterilization cycle selection button (600) is a touch screen element that shows the sterilization cycle type, such as "standard," "duo," "flex," and "express;" and may show additional information such as sterilization cycle duration, a type of biological indicator associated with a sterilization cycle, and other information, for each sterilization cycle selection, as well as instructions for either selecting a cycle or scanning a biological indicator (601). The sterilization cycle selection screen of FIG. 6 also includes a sterilization cycle information button (602) for each sterilization cycle selection, which may be selected by a user to display additional information that may help a user make a sterilization cycle choice. It should be understood that the "standard," "duo," "flex," and "express" sterilization cycles of the present example are merely illustrative. Sterilization cabinet (100) may alternatively offer any other suitable number and types of sterilization cycles for selection.

While FIG. 6 shows each sterilization cycle being associated with a specific type of biological indicator, such as Biological Indicator Apollo Type A, or Biological Indicator Apollo Type B, different embodiments may support different configurations of biological indicator type. In some embodiments, each sterilization cycle may have a different type of biological indicator, such that there may be four or more different types of biological indicator each with a specific application. However, in other embodiments, a single biological indicator may be adapted for use with any sterilization cycle, such that only one type of biological indicator is needed. The number and type of biological indicator required for different sterilization cycle may vary depending upon the desired cost, shelf life, market of sale, or other factors. While the embodiment shown in FIGS. 6 through 18 requires a Type A and Type B indicator, the technology and interfaces shown could be modified to support as few as one type of biological indicator, or as many of a plurality of biological indicator as may be needed.

Figure 7:
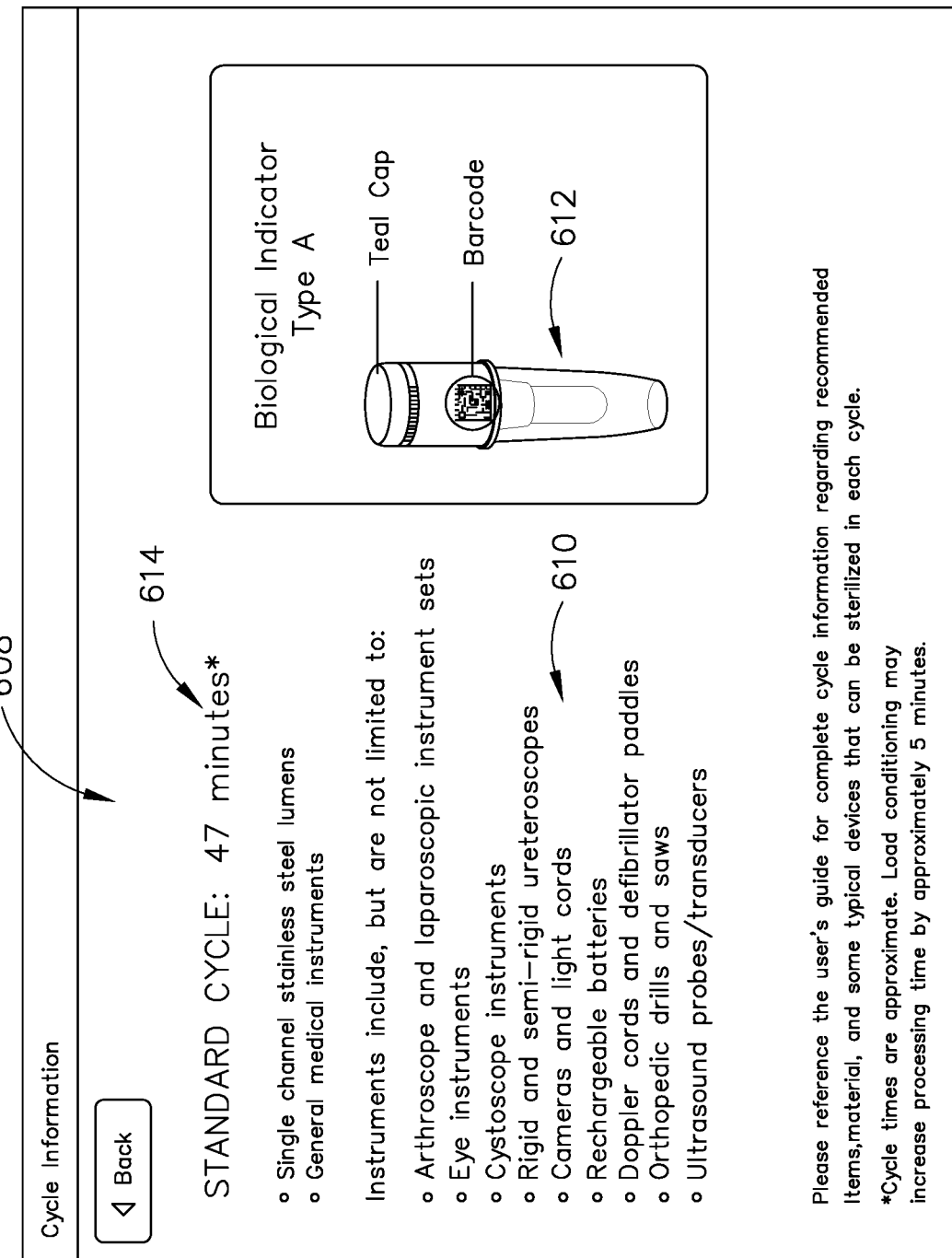
FIG. 7 depicts a screenshot of an exemplary user interface that could be presented via the sterilizing cabinet of the system of FIG. 1, to provide information to a user for configuring a "standard" sterilization cycle.

FIGS. 7-11 show examples of sterilization cycle information screens that may be displayed after interaction with a sterilization cycle information button (602). FIG. 7 shows an exemplary cycle information screen for a "standard" sterilization cycle, which includes a sterilization cycle description (608); a sterilization cycle duration estimate (614); a listing of medical devices (610) suitable for that particular sterilization cycle; and a biological indicator visual aid (612) identifying the type, color, and barcode or identifier location for a biological indicator that is compatible with that particular sterilization cycle. In this particular example, the sterilization cycle description (608) indicates that the "standard" sterilization cycle has a cycle time of approximately 47 minutes; and is intended for instruments including single channel stainless steel lumens and general medical instruments. The listing of medical devices (610) includes the examples of arthroscope and laparascopic instrument sets, eye instruments, cystoscope instruments, rigid and semi-rigid ureteroscopes, cameras and light cords, rechargeable batteries, Doppler cords and defibrillator paddles, orthopedic drills and saws, and ultrasound probes/transducers. The biological indicator visual aid (612) shows that the biological indicator for the "standard" sterilization cycle is a "Type A" biological indicator with a teal cap, though it should be understood that other types, colors, and configurations may also be shown.

Figure 8:
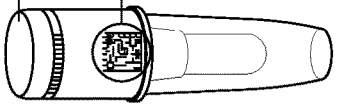
FIG. 8 depicts a screenshot of an exemplary user interface that could be presented via the sterilizing cabinet of the system of FIG. 1, to provide information to a user for configuring a "duo" sterilization cycle.
Figure 9:
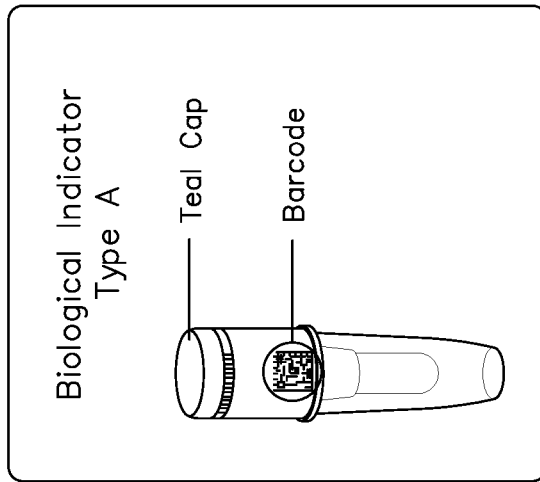
FIG. 9 depicts a screenshot of an exemplary user interface that could be presented via the sterilizing cabinet of the system of FIG. 1, to provide information to a user for configuring a "flex" sterilization cycle.
Figure 10:
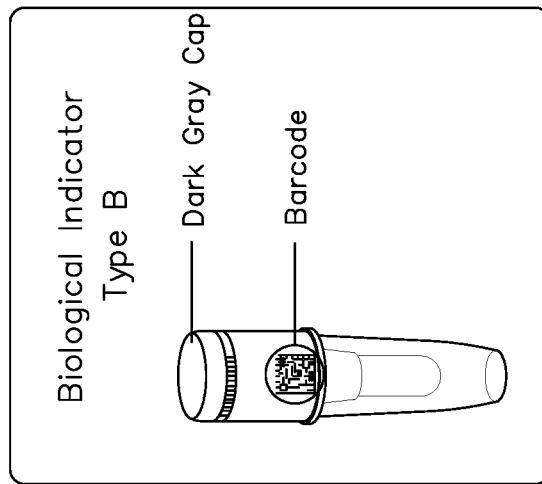
FIG. 10 depicts a screenshot of an exemplary user interface that could be presented via the sterilizing cabinet of the system of FIG. 1, to provide information to a user for configuring a "express" sterilization cycle.

FIGS. 8-10 show similar information for a "duo" sterilization cycle (616), "flex" sterilization cycle (618), and "express" sterilization cycle (620). In particular, in FIG. 8, the sterilization cycle description (616) indicates that the "duo" sterilization cycle has a cycle time of approximately 60 minutes; and is intended for instruments including single channel flexible endoscopes, flexible endoscopes without lumens, cameras, and accessory light cords. The listing of medical devices for the "duo" sterilization cycle includes the examples of bronchoscopes, hysteroscopes, cystoscopes, flexible ureteroscopes, choledochoscopes, thoracoscopes, intubation fiberscopes, light cords, and cameras. The biological indicator visual aid for the "duo" sterilization cycle shows that the biological indicator for the "duo" sterilization cycle is a "Type A" biological indicator with a teal cap, though it should be understood that other types, colors, and configurations may also be shown.

In FIG. 9, the sterilization cycle description (618) indicates that the "flex" sterilization cycle has a cycle time of approximately 42 minutes; and is intended for instruments including single channel flexible endoscopes and flexible endoscopes without lumens. The listing of medical devices for the "flex" sterilization cycle includes the examples of bronchoscopes, hysteroscopes, cystoscopes, flexible ureteroscopes, choledochoscopes, thoracoscopes, and intubation fiberscopes. The biological indicator visual aid for the "flex" sterilization cycle shows that the biological indicator for the "flex" sterilization cycle is a "Type A" biological indicator with a teal cap, though it should be understood that other types, colors, and configurations may also be shown.

In FIG. 10, the sterilization cycle description (620) indicates that the "express" sterilization cycle has a cycle time of approximately 24 minutes; and is intended for general medical devices requiring surface sterilization, sterilization of mated stainless steel, and titanium surfaces. The listing of medical devices for the "express" sterilization cycle includes the examples of da Vinci endoscopes, rigid or semi-rigid endoscopes without lumens, general surgery devices without lumens, rechargeable batteries, eye instruments without lumens, and ultrasound probes/transducers. The biological indicator visual aid for the "express" sterilization cycle shows that the biological indicator for the "flex" sterilization cycle is a "Type B" biological indicator with a dark gray, though it should be understood that other types, colors, and configurations may also be shown.

Sterilization cycle information screens such as those illustrated in FIGS. 8-10 may show additional information, such as pictures and images of medical devices that may be sterilized by the sterilization cycle, sterilization methods used during the sterilization cycle, maximum heat or pressure reached within the sterilization chamber during the sterilization cycle, the number of times the sterilization cycle has been run during a period of time, the last time the sterilization cycle was run, and/or any other information that a user may find useful.

Referring to FIGS. 3 and 6 together, the sterilization cycle selection screen of FIG. 6 may additionally instruct a user to manually select (block 304) a sterilization cycle and/or select and scan a biological indicator (block 302). If a user chooses to scan a biological indicator (block 302) (e.g., using an optical or wireless scanner to scan a barcode, QR code, optical identifier, RFID, or other wireless identifier of a biological indicator), the display may be updated to instead show a filtered selection (block 306) of sterilization cycles that may be selected because they are compatible with the selected and scanned biological indicator (block 302).

In some implementations, interfaces with sterilization cycle selections may be filtered (block 306) based upon a scanned or selected biological indicator (block 302). For example, one interface screen may show that a sterilization cycle associated with a "type B" biological indicator is grayed out and rendered un-selectable. This particular screen may be presented in response to a "type A" biological indicator being selected or scanned (block 304), such that the screen only enables selection of filtered sterilization cycles that are particularly associated with the "type A" biological indicator. As another example, a screen may have the sterilization cycles associated with a "type A" biological indicator grayed out and rendered un-selectable. This particular screen may be presented in response to a "type B" biological indicator being selected or scanned (block 304), such that the screen only enables selection of the filtered sterilization cycle that is particularly associated with the "type B" biological indicator. However, in embodiments that support or require only one type of biological indicator, the process of filtering by supported sterilization cycle type after selecting a biological indicator would not be required.

Referring back to FIGS. 3 and 6 together, a user may not always scan a biological indicator (block 302) before making a sterilization cycle selection. The user may instead make a manual selection (block 304) from any of the displayed sterilization cycle selection buttons (600). After making a manual selection (block 304) of a sterilization cycle, if the user also scanned or selected a biological indicator (block 308) earlier in the process, then the biological indicator may be verified (block 324) for the selected sterilization cycle. Verification (block 324) may include verifying compatibility with system (10) generally, compatibility with the sterilization cycle selected, verifying that the biological indicator is not expired, and/or other verifications.

Some implementations may include screens that may be used to indicate to a user that there is a warning or error related to the biological indicator based upon the verification (block 324). For example, warning messages may be displayed when the biological indicator is from a third party manufacturer where the compatibility of the biological indicator with sterilizing cabinet (100), biological indicator analyzer (102), and/or other devices of system (10) has not been verified or validated. The warning message may include buttons to cancel the use of the biological indicator to give the user a chance to replace the biological indicator with a verified biological indicator (block 326); or bypass the warning and continue to complete the sterilization cycle and indicator selection (block 328).

Some warning messages may be displayed when the identified biological indicator is incompatible with the selected sterilization cycle, such as when a "type A" biological indicator is selected and an "express" sterilization cycle is selected. The warning message may be accompanied by buttons that allow a user to cancel the biological indicator and sterilization cycle selections entirely; or to replace the mismatched biological indicator with a new biological indicator that is compatible with the selected sterilization cycle (block 326). Similarly, another warning may be displayed to indicate to a user that the selected "type B" biological indicator is not valid for use with the selected "standard," "flex," or "duo" sterilization cycle. Again, this warning message may be accompanied by buttons allowing the user to cancel the biological indicator and sterilization cycle selections entirely; or to replace the mismatched biological indicator with a new biological indicator that is compatible with the selected sterilization cycle (block 326). However, in embodiments where only a single type of biological indicator is supported or required, differing warning messages would not be required to indicate a mismatch between a selected cycle and a selected biological indicator.

Some warning messages may be displayed when a user selects or scans a biological indicator that is unidentifiable or entirely incompatible with sterilizing cabinet (100), biological indicator analyzer (102), and/or other devices. These warning messages indicate to the user that the currently selected biological indicator is known to be incompatible and must be replaced with a compatible biological indicator before continuing. These messages may be displayed along with buttons allowing a user to cancel the biological indicator and sterilization cycle selections entirely; or to replace the current biological indicator with a new biological indicator that is compatible with the selected sterilization cycle (block 326).

Some warning messages may be displayed when a user selects or scans a biological indicator that is expired or has been discontinued or recalled. These messages may be accompanied by buttons allowing a user to cancel the biological indicator and sterilization cycle selections entirely; or to replace the expired/discontinued/recalled biological indicator with a new biological indicator (block 326). However, in embodiments where only a single type of biological indicator is supported or required, the warning messages could be consolidated to only require a single biological indicator type.

If, after any of the above warning and error messages, a user selects to continue or bypass the warning, sterilization cabinet (10) will count the biological indicator as having been verified (block 324) despite the warning; and the sterilization cycle selection and biological indicator identification will be complete (block 328). If, after a warning or error, a user chooses to replace (block 326) the previously selected biological indicator with another biological indicator, that newly selected biological indicator may be verified (block 324). If there are no warnings or errors based on the newly selected biological indicator, the sterilization cycle selection and biological indicator identification is complete (block 328).

If no biological indicator is scanned (block 308) prior to a manual selection (block 304) of a sterilization cycle, sterilization cabinet (100) will determine if there is a hard requirement (block 310) or soft requirement (block 314) for using a biological indicator. Determination of whether there is a hard requirement (block 310) or soft requirement (block 314) may depend upon a variety of configurable factors that may vary depending upon a particular hospital where system (10) is used, a particular geographical region in which system (10) is used, a user's insurance carrier requirements, and/or various other factors.

For example, in some versions there may be a hard requirement (block 310) that requires that a biological indicator be used in certain circumstances in order to comply with a rule, law, or other regulation. If such a hard requirement applies to the current sterilization cycle that is being configured (block 310), the hard indicator requirements may be displayed (block 312) since a user has not yet scanned or selected a biological indicator (308). In some implementations, a screen may be displayed when a hard requirement applies (block 310) to the selected sterilization cycle. For example, a hard requirement description may indicate to the user the circumstances of the particular hard requirement that applies (block 310); and a biological indicator guide may show a graphical representation of the biological indicator that is required to continue. This screen may be accompanied by a button that allows a user to cancel the selection process entirely. However, such a screen does not have a button that would allow the user to bypass the requirement or continue in the absence of an appropriate biological indicator.

As another example, a screen may show that the system requires a "type B" biological indicator in order to continue the process. The hard requirement screens may show additional information, such as a contact number or information for individuals that can provide support, such as technical support personnel for sterilizing cabinet (100), the biological indicator, the hospital where sterilizing cabinet (100) is located, and/or other individuals that might be able to provide assistance when a user unexpectedly receives a hard requirement (block 310). However, in embodiments that only support or require a single biological indicator type, only a single interface may be needed to show a requirement for a single biological indicator.

While some hard requirement may be a "once per 24 hours" requirement, other requirements may exist. For example, in some versions there may be a hard requirement to use a biological indicator for every cycle, every other cycle, every X number of cycles, a certain number of times per day, a certain number of times per period of hours, and/or other scenarios as may be configured.

While a hard requirement is intentionally designed to appear as being impassable without the selection of an appropriate biological indicator, some versions of system (10) may also be configured to display a set of hard requirement bypass screens to allow users to bypass (block 320) even a hard requirement in case of emergency or other substantial need. Such a screen may be configured to receive a pass code, supplied by support personnel or hospital administrators that will allow the hard requirement to be bypassed. Such a screen may be followed by a screen that indicates to a user that the pass code was accepted, and may disable hard requirements during sterilization cycle configuration for a certain number of sterilization cycles; or for a certain period of time.

Referring back to FIG. 3, if the hard bypass is successful (block 320), the sterilization cycle selection and biological indicator identification is complete (block 328). Bypassing a hard requirement may result in additional alerts or notifications being sent to hospital administrators or other responsible individuals, and may transmit additional information to server (106) indicating the particular circumstances of the hard bypass (block 320) so that the event can be examined at a later time. A code bypass is one example of a hard requirement bypass (block 320), but other embodiments exist. For example, hard requirement bypass (block 320) may also be accomplished by scanning of an optical barcode, RFID tag, or other indicator that may be held by a small group of individuals within a hospital; or scanning of a dummy indicator that allows for a single bypass or limited number of bypasses.

Figure 11:
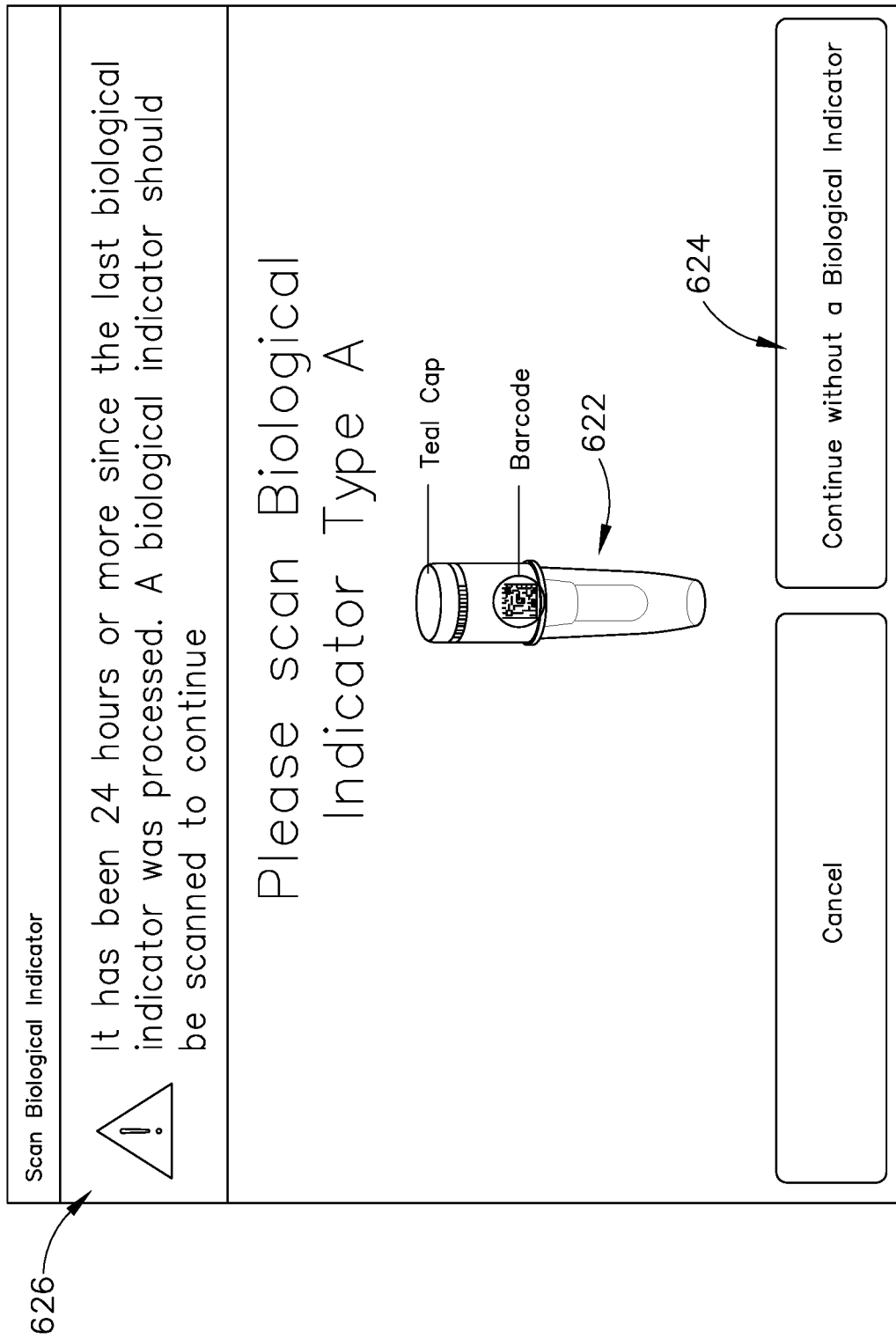
FIG. 11 depicts a screenshot of an exemplary user interface that could be presented via the sterilizing cabinet of the system of FIG. 1, to present a user with a soft requirement for selecting a biological indicator for use with a selected sterilization cycle.

If there is no hard requirement (block 310), sterilization cabinet (100) will determine if there is a soft requirement (block 314). A soft requirement may conditionally apply in similar circumstances as the hard requirement, such as for every sterilization cycle, intermittent sterilization cycles, intermittent time periods, or other scenarios. If a soft requirement exists (block 314), the soft biological indicator requirement may be displayed (block 316) via a screen such as that shown in FIG. 11. FIG. 11 shows a soft requirement description (626), a biological indicator visual guide (622), and a soft bypass (624) button. The soft requirement description (626) indicates that it has been 24 hours or more since the last biological indicator was processed, such that a new biological indicator should be scanned to continue. A user may cancel the cycle, or may choose the soft bypass (624) button if they do not wish to select a biological indicator. If the soft bypass is selected block (318), the sterilization cycle selection and indicator identification is complete (block 328). Additionally, if there is no hard requirement (block 310) and no soft requirement (block 314), the user may proceed with no biological indicator and no need for bypass; and the sterilization cycle selection and biological indicator identification is complete (block 328).

If no biological indicator is scanned prior manual selection of the sterilization cycle (block 304), and a hard or soft requirement exists (block 310, block 314) and is not bypassed (block 318, block 320), the user must scan a biological indicator (block 308) before sterilization cabinet (100) will proceed. Once a biological indicator is scanned (block 308), biological indicator verification (block 324) will proceed as previously described. In the event that either a soft or hard bypass is used (block 318, block 320), an additional warning may be displayed to notify the user of the requirement for using a biological indicator.

C. Exemplary Medical Device Placement and Load Conditioning Process

Figure 4:
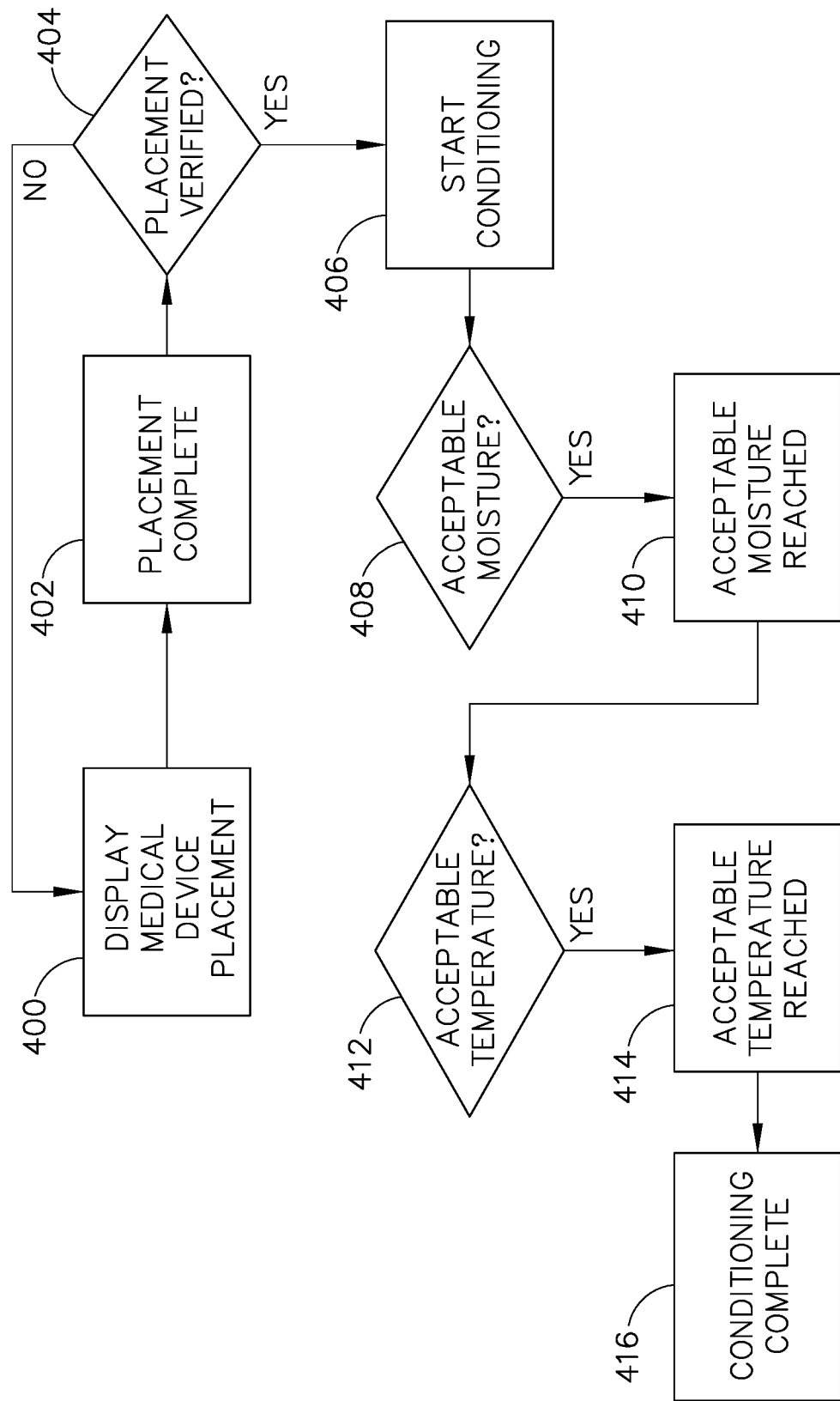
FIG. 4 depicts a flowchart of an exemplary set of steps that the sterilizing cabinet of the system of FIG. 1 could perform to prepare medical devices for a sterilization cycle.

FIG. 4 depicts an exemplary set of steps that sterilizing cabinet (100) could perform to guide a user through placement of medical devices in the sterilizing chamber of sterilizing cabinet (100) and prepare the medical devices for a sterilization cycle. It should be understood that the method shown in FIG. 4 may be viewed as showing several sub-steps that may be performed as part of the sterilization cycle preparation step (block 204) and the load conditioning step (block 206) of FIG. 2.

Once the sterilization cycle has been selected (block 200) and the biological indicator has been identified (block 202), sterilizing cabinet (100) may display (block 400) a medical device placement that serves as a visual guide to a user's placement of medical devices within the sterilizing chamber of sterilizing cabinet (100), based on the selected sterilization cycle (block 200). Some implementations may include screens that may be used to display (block 400) medical device placement.

Figure 12:
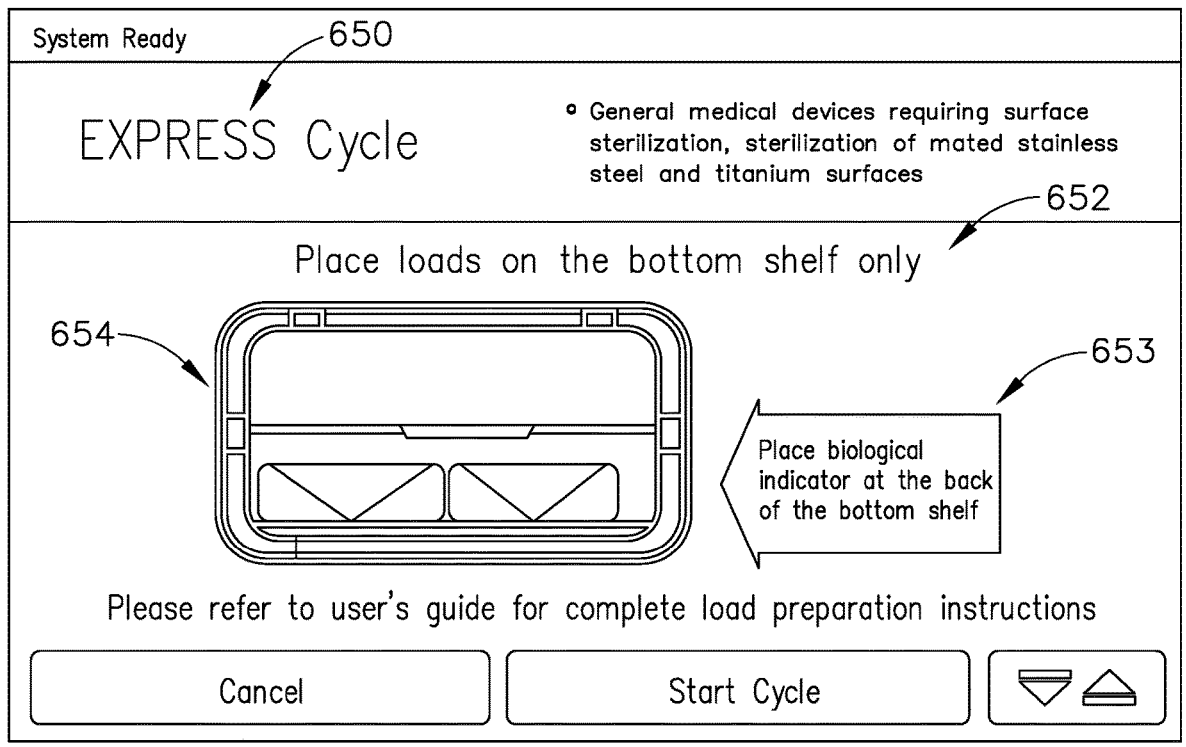
FIG. 12 depicts a screenshot of an exemplary user interface that could be presented via the sterilizing cabinet of the system of FIG. 1, to guide a user through placement and configuration of medical devices for an "express" sterilization cycle.
Figure 13:
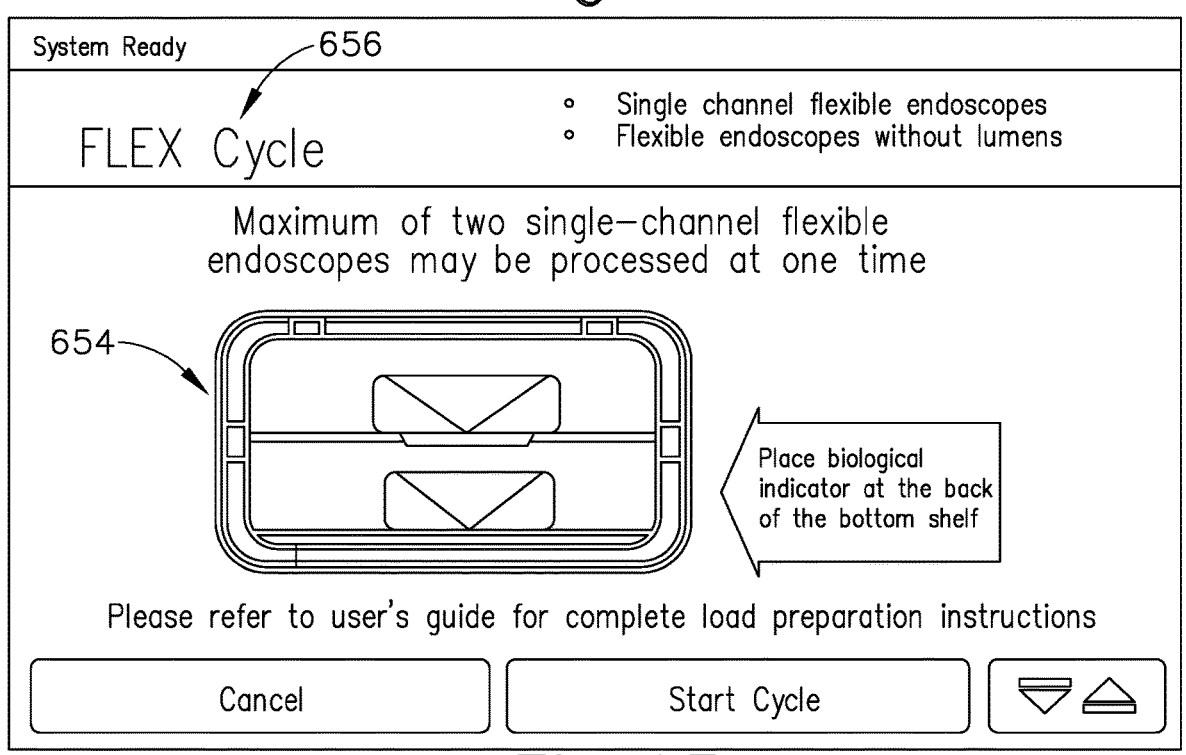
FIG. 13 depicts a screenshot of an exemplary user interface that could be presented via the sterilizing cabinet of the system of FIG. 1, to guide a user through placement and configuration of medical devices for a "flex" sterilization cycle.
Figure 14:
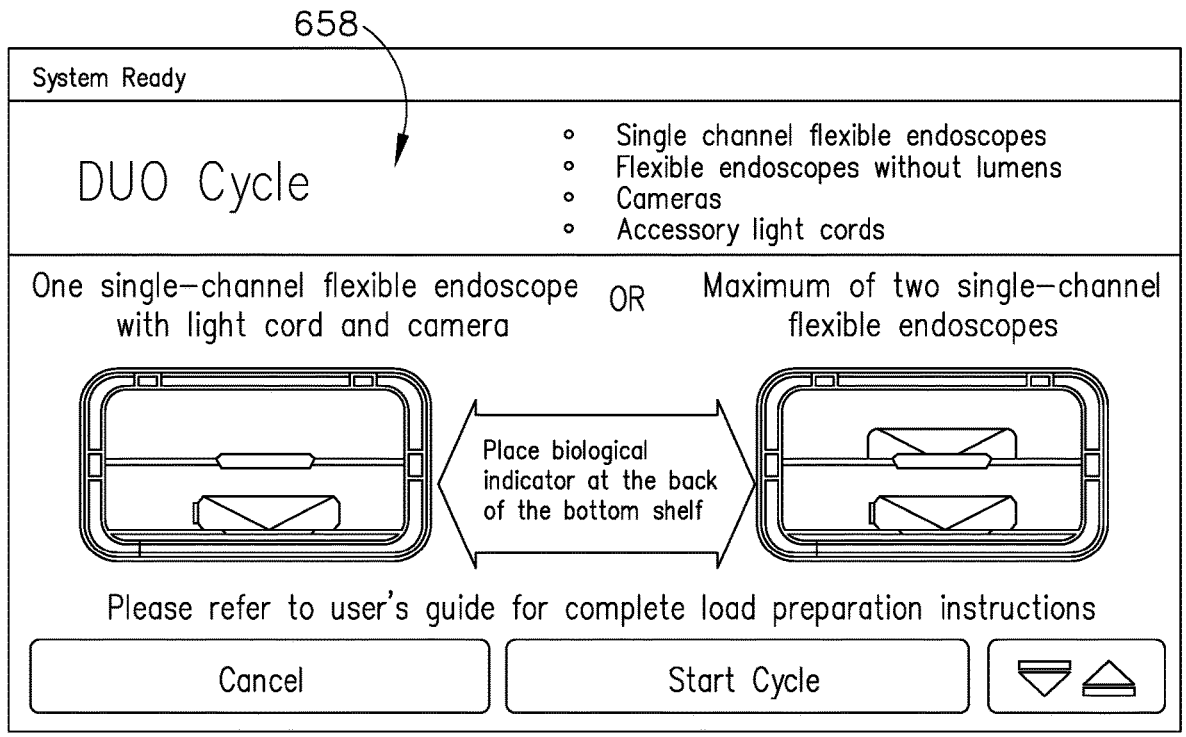
FIG. 14 depicts a screenshot of an exemplary user interface that could be presented via the sterilizing cabinet of the system of FIG. 1, to guide a user through placement and configuration of medical devices for a "duo" sterilization cycle.
Figure 15:
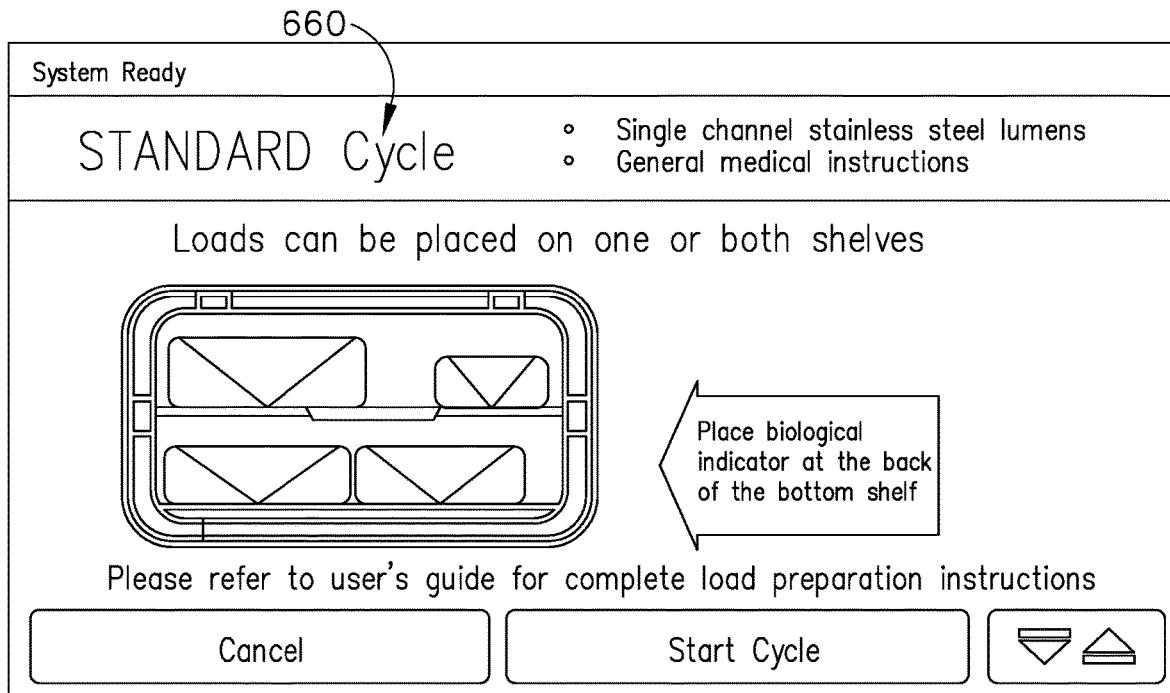
FIG. 15 depicts a screenshot of an exemplary user interface that could be presented via the sterilizing cabinet of the system of FIG. 1, to guide a user through placement and configuration of medical devices for a "standard" sterilization cycle.

FIG. 12 shows an interface having a cycle description (650) that may describe one or more characteristics of the medical sterilization devices sterilized by the sterilization cycle, materials sterilized by the sterilization cycle, or processes used during the sterilization cycle. The interface may also have one or more placement instructions (652) that provide the user with instructions on where to place medical instruments that are to be sterilized (e.g., in relation to a shelf in the sterilization chamber), as well as where to place the biological indicator (653), if applicable to the selected sterilization cycle. The interface may also have a graphical indication (654) of placement of medical devices that may have a shape or appearance that is visually similar to a sterilization chamber of sterilizing cabinet (100). FIG. 13 shows a similar interface that provides a visual placement guide for a "flex" cycle (656), while FIG. 14 shows a similar interface for a "duo" cycle (658), and FIG. 15 shows a similar interface for a "standard" cycle (660).

Referring back to FIG. 4, once medical device placement is complete (block 402), the user may press a start button or other button indicating that medical device placement is complete and sterilizing cabinet (100) may verify medical device placement (block 404). Placement verification may occur in varying ways depending upon a particular embodiment. In some versions, placement verification may simply be a final display and confirmation of the visual placement guide (654). In other versions, placement verification may be by way of imaging devices or photo sensors, weight sensors, two-dimensional or three-dimensional camera image capture and comparison, or similar types of sensors that may detect the physical presence of an object within a defined space by way of recognizing one or more physical characteristics of its presence.

Placement verification (block 404) could also be accomplished by way of a wireless RFID or NFC scanner and placement of an RFID or NFC chip on medical devices, either at the time of manufacture, the time of use, or sterilization. One or more wireless scanners could be placed in walls of sterilizing cabinet (100) and could be configured to, at the time of verification (block 404), identify the locations of medical devices within the sterilization chamber and verify that they are within a configured distance of the scanner. Versions having a wireless scanner could further be configured to identify placement of medical devices as well as types of medical devices, which could be used as an additional confirmation that the proper sterilization cycle is selected for the types of medical devices placed in the sterilization chamber.

If medical device placement cannot be verified (block 404), the cycle placement guide may be displayed again (block 400). If medical device placement is verified (block 404), sterilizing cabinet (100) may start a load conditioning process (block 406). The load conditioning process (block 406) prepares the sterilization chamber and the medical devices within the sterilization chamber for optimal sterilization during a sterilization cycle. Conditioning may include controlling and optimizing one or more characteristics of the sterilization chamber. For example, during load conditioning, sterilizing cabinet (100) may continuously monitor the level of moisture (block 408) within the sterilization chamber while reducing the level of moisture by, for example, circulating and dehumidifying the air of the sterilization chamber, creating a vacuum within the sterilization chamber, heating the sterilization chamber, and/or other methods for dehumidifying a sealed chamber. This may continue until sterilizing cabinet (100) determines that an acceptable level of moisture has been reached (block 410).

Sterilizing cabinet (100) may also continuously detect the temperature (block 412) within the sterilization chamber while heating the sterilization chamber by, for example, convection of heated air, conduction through an interior surface of the sterilization chamber, and/or using other techniques. This may continue until sterilizing cabinet (100) determines that an acceptable internal temperature has been reached (block 414). Various conditioning actions such as controlling temperature or humidity may be performed in parallel or in sequence. While the one or more conditioning actions are being performed, sterilizing cabinet (100) may display an interface indicating to a user the duration of time before the sterilization cycle performance may begin. Once all load conditioning criteria have been successfully met, load conditioning is complete (block 416) and the sterilization cycle may then be performed (block 208). It should therefore be understood that sterilizing cabinet (100) is configured such that the sterilization cycle (block 208) is not actually initiated until after the load conditioning process (block 206) is complete.

Load conditioning (block 206) may not always be possible, due to system error, abnormally high moisture levels, or abnormally low temperatures. Some implementations may include an interface that may be displayed when attempts to reduce moisture fail or other general errors occur during load conditioning. The interface provides additional guidance to a user so that further attempts to conditioning may be made. Another interface may be displayed when sterilization chamber temperatures are not able to be raised to an acceptable range, and may indicate to a user the reason for the failure.

As noted above, sterilization cabinet (100) may begin performing the sterilization cycle (block 208) automatically and immediately after load conditioning (block 206) has been completed. During performance of the sterilization cycle (block 208), an interface may be displayed that shows a duration remaining for cycle, an overall cycle completion, and a current cycle stage, which describes what part of the sterilization cycle is currently being performed (e.g. plasma, vacuum, injection, heat, chemical treatment), in addition to buttons for canceling the sterilization cycle and viewing further information on the sterilization cycle.

D. Exemplary Reporting of Sterilization Cycle Results

Figure 5:
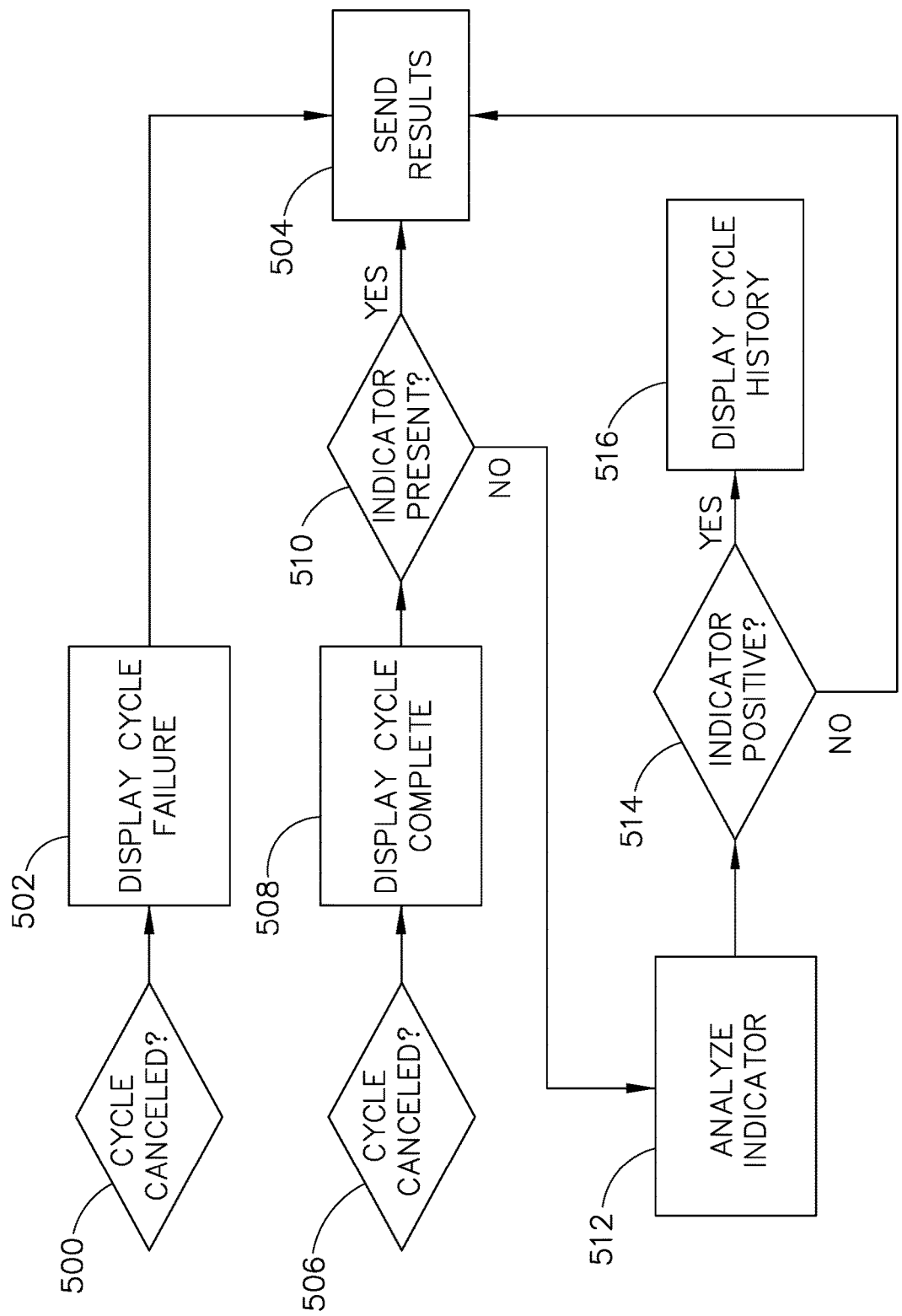
FIG. 5 depicts a flowchart of an exemplary set of steps that the sterilizing cabinet of the system of FIG. 1 could perform to complete and report results for a sterilization cycle.

FIG. 5 depicts an exemplary set of steps that sterilizing cabinet (100) could perform to complete and report results of a sterilization cycle upon completion of the cycle (block 208). In other words, the method shown in FIG. 5 may be viewed as showing several sub-steps that may be performed as part of the provision of results step (block 210) of FIG. 2. If the sterilization cycle was canceled or unable to complete due to error or by a user action (block 500), sterilizing cabinet (100) may remain sealed and may also display (block 502) an interface which shows a sterilization cycle cancellation message as well as various details relating to the sterilization cycle, such as date, time, configuration, elapsed time, sterilization cycle operator, the stage at which the sterilization cycle failed, and other information that may be used to identify why the sterilization cycle failed. Such displayed information and other information relating to the sterilization cycle may also be sent (block 504) to the server (106) or to a printer, or both, for further use or analysis.

Figures 16, 17:
FIG. 16 depicts a screenshot of an exemplary user interface that could be presented via the sterilizing cabinet of the system of FIG. 1, to deliver results to a user for a completed sterilization cycle.
FIG. 17 depicts a screenshot of an exemplary user interface that could be presented via the sterilizing cabinet of the system of FIG. 1, to identify cycles associated with a positive biological indicator result as communicated from an indicator analyzer of the system of FIG. 1 via a communication hub of the system of FIG. 1.

If the sterilization cycle completes (block 506), sterilization cabinet (100) may display a sterilization cycle complete (block 508) interface such as that shown in FIG. 16, which may include information such as sterilization cycle identifier, sterilization cycle type, start time, duration, operator, and other information (666). If a biological indicator is not present (block 510) during the sterilization cycle, the displayed information and other information associated with the sterilization cycle may be sent (block 504) to the server (106) or to a printer, or both, for further use or analysis. If a biological indicator was selected and used (block 510) during the sterilization cycle, the biological indicator may be removed by the user and placed in biological indicator analyzer (102) to determine the efficacy of the sterilization treatment (block 512), as described in greater detail below.

If data provided by biological indicator analyzer (102) indicates that the biological indicator tests negative for contamination (block 514), the results of the sterilization cycle as well as the results of the indicator analysis (block 512) are sent (block 504) to server (106) or a printer, or both. If data provided by biological indicator analyzer (102) suggests that the biological indicator tests positive for contamination (block 514), sterilization cabinet (100) may display the sterilization cycle history (block 516) for sterilization cycles occurring before the immediate sterilization cycle so that a user may determine if any prior performed sterilization cycles may need to be re-run to ensure the sterility of the medical devices involved. If subsequent sterilization cycles were performed after the above-described sterilization cycle and before the biological indicator analysis (block 512) is complete, those subsequent sterilization cycles may also need to be re-run.

FIG. 17 shows an example of an interface for displaying sterilization cycle history of potentially affected sterilization cycles to a user in the event of a positive biological indicator result (block 514). The example interface of FIG. 17 shows the biological indicator result (668); a biological indicator identifier (670), which relates a unique biological indicator to the sterilization cycle for which it was selected or scanned, a time at which the biological indicator was analyzed (672); as well as a previous sterilization cycle window, which shows a sequential listing of the previously performed sterilization cycles (674) that may be affected, which goes back at least as far as the previously performed sterilization cycle which included a biological indicator; a sterilization cycle completion time for each affected sterilization cycle (676); a sterilization cycle type for each affected sterilization cycle (678); and a biological indicator result for each affected sterilization cycle (680).

The interface of FIG. 17 could be used by a user to identify a set of affected sterilization cycles, which in some cases will be each sterilization cycle that was performed (i) prior to the sterilization cycle that generated a positive indication of contamination and (ii) subsequent to the most recent sterilization cycle that generated a negative indication of contamination. This set of affected sterilization cycles provides a narrow listing of each sterilization cycle that may not have been fully effective as a result of a change in performance of sterilizing cabinet (100) or other error or contamination that also may have caused the current positive indication of contamination. Medical devices that were believed to be sterilized during the affected sterilization cycles may be reexamined and/or re-sterilized in order to ensure safe use.

III. Exemplary Sterilizing Cabinet

Figure 18:
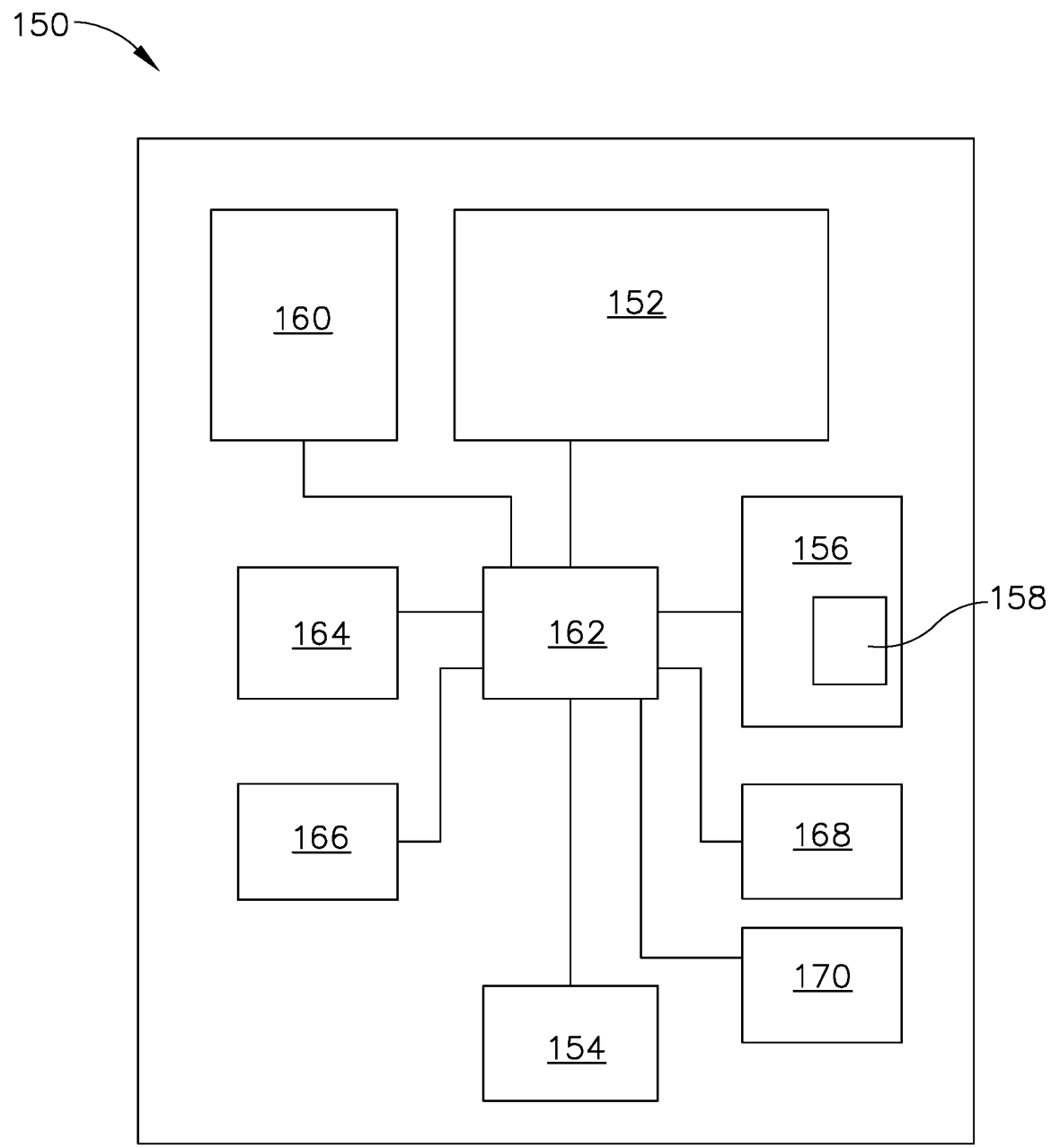
FIG. 18 depicts a schematic view of an exemplary sterilizing cabinet that may be used with the system of FIG. 1.

FIG. 18 depicts an exemplary set of components that may be incorporated into sterilizing cabinet (100) of system (10). In particular, FIG. 18 shows an exemplary sterilizing cabinet (150) that is operable to perform the various methods described above and shown in FIGS. 2-5. Sterilizing cabinet (150) of the present example includes a sterilization chamber (152), which is configured to receive one or more medical devices for sterilization. While not shown, sterilizing cabinet (150) also includes a door that opens and closes sterilization chamber (152) in response to actuation of a kick plate (154). An operator may thereby open and close sterilization chamber (152) in a hands-free fashion. Sterilizing cabinet (100) also includes a sterilization module (156) that is operable to dispense a sterilant into sterilization chamber (152) in order to sterilize medical devices contained in sterilization chamber (152) as described above. In the present example, sterilization module (156) is configured to receive replaceable sterilant cartridges (158) containing a certain amount of sterilant. By way of example only, each sterilant cartridge (158) may contain enough sterilant to perform five sterilization procedures.

Sterilizing cabinet (150) of the present example further includes a touch screen display (160). Touch screen display (160) is operable to render the various user interface display screens described above and shown in FIGS. 6-18. Of course, touch screen display (160) may display various other screens as well. Touch screen display (160) is further configured to receive user input in the form of the user contacting touch screen display (160) in accordance with conventional touch screen technology. In addition or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). As will be described in greater detail below and as shown in FIG. 18, processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes a communication module (164). Communication module (164) is configured to enable bidirectional communication between sterilizing cabinet (150) and communication hub (104). In addition or in the alternative, communication module (164) may be configured to enable bidirectional communication between sterilizing cabinet (150) and server (106). By way of example only, communication module (164) may be configured to provide wired and/or wireless communication via as Ethernet, Wi-Fi, Bluetooth, USB, infrared, NFC, and/or other technologies. Various suitable components and configurations that may be used to form communication module (164) will be apparent to those of ordinary skill in the art in view of the teachings herein. Communications that are sent from or received through communication module (164) are processed through processor (162).

Sterilizing cabinet (150) of the present example further includes a reader (166), which is operable to read an identification tag of a biological indicator as described herein. It should be understood that reader (166) may be used to perform the steps of indicator scanning (block 302, block 308) described above with reference to FIG. 3. By way of example only, reader (166) may comprise an optical reader that is operable to read an optical identification tag (e.g., barcode, QR code, etc.) of a biological indicator. In addition or in the alternative, reader (166) may comprise RFID reader that is operable to read an RFID identification tag (e.g., barcode, QR code, etc.) of a biological indicator. Various suitable components and configurations that may be used to form reader (166) will be apparent to those of ordinary skill in the art in view of the teachings herein. Data received through reader (166) is processed through processor (162).

Sterilizing cabinet (150) of the present example further includes a memory (168), which is operable to store control logic and instructions and that are executed by processor (162) to drive components such as sterilization module (156), touch screen display (160), communication module (164), and reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; and/or U.S. Pat. No. 6,447,719, the disclosure of which is incorporated by reference herein.

IV. Exemplary Biological Indicator Assembly

As noted above, a biological indicator may be included in sterilizing cabinet (100, 150) along with the medical device during the sterilization process (block 208) in order to ensure that the sterilization process (block 208) was successful. An exemplary biological indicator includes a housing, a cap, an ampoule, and a carrier. The housing is formed of a transparent material (e.g., clear plastic, glass, etc.) and is hollow such that the housing insertably receives the ampoule. The ampoule is also formed of a transparent material (e.g., clear plastic, glass, etc.) and contains a fluid. By way of example only, the fluid may comprise a liquid growth medium that is capable of, with incubation, promoting growth of any viable microorganisms it contacts. The fluid also includes a fluorophore whose fluorescence depends on the amount of microorganisms contained in the medium. The fluid is sealed within the ampoule.

A carrier provides a source of microorganisms or active enzymes. By way of example only, a carrier may be impregnated with bacterial spores, other forms of bacteria (e.g., vegetative), and/or active enzymes. By way of example only, spores from Bacillus, Geobacillus, and Clostridium species may be used. Various suitable ways in which the carrier may be constructed will be apparent to those of ordinary skill in the art in view of the teachings herein.

The ampoule is configured as a frangible component of the biological indicator, such that the ampoule may be fractured within housing to release a fluid in the housing. To assist in the fracture of the ampoule, a cap is configured to slide downwardly along the housing to press the ampoule against fracturing features. This may be done right before a biological indicator is inserted into indicator analyzer (102). It should be understood that the ampoule would remain intact while the biological indicator is in sterilizing cabinet (100) during a sterilization process. The cap may include one or more openings that allow gasses (e.g., air or sterilant, etc.) to pass into the housing before the cap is pressed downwardly relative to the housing to fracture the ampoule. These openings may thus enable the microorganisms on a carrier to be destroyed by the sterilization process (block 208). However, after the cap is pressed downwardly relative to the housing to fracture the ampoule, these one or more openings may be sealed to contain the released fluid in the housing. When the fluid is released from the ampoule, the released fluid eventually reaches the carrier, thereby initiating an incubation process with any living microorganisms remaining on the carrier, as will be described in greater detail below.

The housing may also include an identification tag. Such an identification tag may include a machine readable feature that is capable of being read by reader (166) of sterilizing cabinet (100, 150) and indicator analyzer (102). In other words, the identification tag may be read perform to the steps of indicator scanning (block 302, block 308) described above with reference to FIG. 3. By way of example only, the identification tag may comprise an optical code (e.g., a barcode, a QR code, etc.), an RFID tag, and/or any other suitable kind of machine readable identifier. In addition, the identification tag may include human readable features such as text, numbers, color coding, etc.

In addition to or in lieu of the foregoing, a biological indicator may be configured and operable in accordance with at least some of the teachings of U.S. patent application Ser. No. 15/057,768, entitled "Self-Contained Biological Indicator," filed Mar. 1, 2016, the disclosure of which is incorporated by reference herein. Other suitable forms that a biological indicator may take will be apparent to those of ordinary skill in the art in view of the teachings herein.

V. Exemplary Biological Indicator Analyzer

An exemplary biological indicator analyzer (102) may be operable to perform the biological indicator analysis (block 512) described above with reference to FIG. 5. The biological indicator analyzer (102) of this example comprises a plurality of wells, each of which is configured to insertingly receive a respective biological indicator. The biological indicator analyzer (102) also includes a processor that is operable to execute instructions and control algorithms, process information, etc.

Each well has an associated light source and sensor. Each light source is configured to project light through the housing of the biological indicator that is inserted in the corresponding well; and each sensor is operable to detect light fluoresced by fluid contained in the housing. As noted above, the fluorescence of fluid will depend on the amount of living microorganisms contained in the medium of the fluid. Thus, the sensor will be able to detect the presence of living microorganisms in the fluid based on the degree to which fluid fluoresces in response to light from light source.

The biological indicator analyzer (102) of the present example further includes a touch screen display. The touch screen display is operable to render various user interface display screens associated with operation of a biological indicator analyzer (102). The biological indicator analyzer (102) of the present example further includes a communication module. The communication module is configured to enable bidirectional communication between the biological indicator analyzer (102) and the communication hub (104). In addition or in the alternative, the communication module may be configured to enable bidirectional communication between a biological indicator analyzer (102) and a server (106). Various suitable components and configurations that may be used to form the communication module will be apparent to those of ordinary skill in the art in view of the teachings herein.

The biological indicator analyzer (102) of the present example further includes a reader, which is operable to read an identification tag of the biological indicator as described herein. It should be understood that the reader may be used to identify a biological indicator before the biological indicator is analyzed (block 512). By way of example only, the reader may comprise an optical reader that is operable to read an optical identification tag (e.g., barcode, QR code, etc.) of a biological indicator. In addition or in the alternative, a reader may comprise RFID reader that is operable to read an RFID identification tag (e.g., barcode, QR code, etc.) of a biological indicator. Various suitable components and configurations that may be used to form a reader will be apparent to those of ordinary skill in the art in view of the teachings herein.

By way of further example only, biological indicator analyzer (102) may be constructed and operable in accordance with at least some of the teachings of U.S. Provisional Patent Application No. 62/316,722, entitled "System and Method for Sterilizing Medical Devices," filed Apr. 1, 2016, the disclosure of which is incorporated by reference herein. Other suitable forms that biological indicator analyzer (102) may take will be apparent to those of ordinary skill in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A system comprising: (a) a sterilizing cabinet, wherein the sterilizing cabinet includes a sterilization chamber, wherein the sterilizing cabinet is operable to sterilize a medical device disposed in the sterilization chamber; (b) a biological indicator analyzer, wherein the biological indicator analyzer is operable to detect the presence of a living organism in a biological indicator assembly; and (c) a communication hub, wherein the sterilizing cabinet is in communication with the communication hub, wherein the biological indicator analyzer is also in communication with the communication hub, wherein the communication hub is operable to transmit information from the biological indicator analyzer to the sterilizing cabinet.

EXAMPLE 2

The system of Example 1, further comprising a server, wherein the server is in communication with the communication hub.

EXAMPLE 3

The system of Example 2, wherein the communication hub is operable to transmit information from the biological indicator analyzer to the server.

EXAMPLE 4

The system of any one or more of Examples 2 through 3, wherein the communication hub is operable to transmit information from the sterilizing cabinet to the server.

EXAMPLE 5

The system of any one or more of Examples 2 through 4, wherein the communication hub is operable to transmit information from the server to the sterilizing cabinet.

EXAMPLE 6

The system of any one or more of Examples 2 through 4, wherein the communication hub is operable to transmit information from the server to the biological indicator analyzer.

EXAMPLE 7

A sterilizing cabinet, wherein the sterilizing cabinet includes a sterilization chamber, wherein the sterilizing cabinet is operable to sterilize a medical device disposed in the sterilization chamber, wherein the sterilizing cabinet is further operable to condition the medical device before sterilizing the medical device.

EXAMPLE 8

The sterilizing cabinet of Example 7, wherein the sterilizing cabinet is operable to condition the medical device before sterilizing the medical device by detecting moisture on the medical device and removing the moisture from the medical device.

EXAMPLE 9

A sterilizing cabinet, comprising: (a) a sterilization chamber, wherein the sterilizing cabinet is operable to sterilize a medical device disposed in the sterilization chamber; and (b) a reader, wherein the reader is operable read an identification tag of a biological indicator.

EXAMPLE 10

The sterilizing cabinet of Example 9, wherein the reader is operable to scan an optical code on the biological indicator.

EXAMPLE 11

The sterilizing cabinet of any one or more of Examples 9 through 10, further comprising a graphical user interface, wherein the graphical user interface is configured to prompt a user to operate the reader to read an identification tag of a biological indicator.

EXAMPLE 12

The sterilizing cabinet of Example 11, wherein the graphical user interface is further configured to prompt a user to select a sterilization cycle from a plurality of available sterilization cycles.

EXAMPLE 13

The sterilizing cabinet of Example 12, wherein the sterilizing cabinet is configured to identify a particular kind of biological indicator associated with a particular sterilization cycle selected by the user, wherein the graphical user interface is further configured to prompt a user to operate the reader to read an identification tag of the particular kind of biological indicator associated with a particular sterilization cycle selected by the user.

EXAMPLE 14

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to place the medical device and the identified biological indicator into a sterilization chamber of a sterilizing cabinet; (d) performing load conditioning on the medical device in the sterilization chamber, wherein the act of performing load conditioning comprises removing moisture from the medical device; and (e) performing the selected sterilization cycle on the medical device in the sterilization chamber after completing the act of load conditioning.

EXAMPLE 15

The method of Example 14, further comprising prompting the user to scan an identification tag of the identified biological indicator before prompting the user to place the medical device and the identified biological indicator into the sterilization chamber.

EXAMPLE 16

The method of Example 15, further comprising evaluating a facility policy regarding use of biological indicators, wherein the act of prompting the user to scan an identification tag of the identified biological indicator is performed based on the evaluation of the facility policy regarding the user of biological indicators.

EXAMPLE 17

The method of any one or more of Examples 15 through 16, wherein the sterilizing cabinet has a graphical user interface, wherein the act of prompting the user to scan an identification tag of the identified biological indicator is performed through the graphical user interface.

EXAMPLE 18

The method of any one or more of Examples 14 through 17, wherein the sterilizing cabinet has a touch screen.

EXAMPLE 19

The method of Example 18, wherein the input from the user selecting the particular sterilization cycle is received via the touch screen.

EXAMPLE 20

The method of any one or more of Examples 18 through 19, wherein the act of prompting the user to place the medical device and the identified biological indicator into a sterilization chamber of a sterilizing cabinet is performed via the touch screen.

EXAMPLE 21

The method of any one or more of Examples 18 through 20, further comprising presenting the user with information regarding each of the available sterilization cycles via the touch screen.

EXAMPLE 22

The method of any one or more of Examples 18 through 21, further comprising presenting the user with information regarding the completed sterilization cycle after performing the selected sterilization cycle on the medical device, wherein the act of presenting the user with information regarding the completed sterilization cycle is performed via the touch screen.

EXAMPLE 23

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to use a reader of a sterilizing cabinet to read an identification tag of the identified kind of biological indicator; (d) receiving information from the reader based on the user's use of the reader to read an identification tag of a biological indicator; (e) prompting the user to place the medical device and the identified biological indicator into a sterilization chamber of the sterilizing cabinet; and (f) performing the selected sterilization cycle on the medical device in the sterilization chamber.

EXAMPLE 24

The method of Example 23, further comprising performing load conditioning on the medical device in the sterilization chamber, wherein the act of performing load conditioning comprises removing moisture from the medical device.

EXAMPLE 25

The method of Example 24, wherein the act of performing the selected sterilization cycle is performed after completing the act of load conditioning.

EXAMPLE 26

The method of any one or more of Examples 23 through 25, further comprising determining whether the information received from the reader indicates that the user has selected the particular kind of biological indicator associated with the selected sterilization cycle.

EXAMPLE 27

The method of Example 26, wherein the act of determining indicates that the user has not selected the particular kind of biological indicator associated with the selected sterilization cycle, the method further comprising informing the user that the user has not selected the particular kind of biological indicator associated with the selected sterilization cycle.

EXAMPLE 28

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to place the medical device and the identified biological indicator into a sterilization chamber of the sterilizing cabinet; (d) performing the selected sterilization cycle on the medical device in the sterilization chamber; and (e) determining whether the identified biological indicator contains any living organisms after performing the selected sterilization cycle.

EXAMPLE 29

The method of Example 28, wherein the act of determining whether the identified biological indicator contains any living organisms comprises evaluating fluorescence associated with the identified biological indicator.

EXAMPLE 30

The method of any one or more of Examples 28 through 29, wherein the act of determining whether the identified biological indicator contains any living organisms indicates that the identified biological indicator contains a living organism, the method further comprising informing the user that the identified biological indicator contains a living organism.

EXAMPLE 31

The method of Example 30, wherein the act of informing the user that the identified biological indicator contains a living organism is performed via the sterilizing cabinet.

EXAMPLE 32

The method of any one or more of Examples 28 through 31, wherein the act of determining whether the identified biological indicator contains any living organisms is performed using a biological indicator analyzer, wherein the biological indicator analyzer is separate from the sterilizing cabinet.

EXAMPLE 33

A method of processing a medical device, the method comprising: (a) receiving input from a user selecting a sterilization cycle from a plurality of available sterilization cycles; (b) identifying a biological indicator associated with the selected sterilization cycle; (c) prompting the user via a touch screen display to place the medical device and the biological indicator into a sterilization chamber of a sterilizing cabinet; (d) performing load conditioning on the medical device in the sterilization chamber; and (e) performing the selected sterilization cycle on the medical device in the sterilization chamber after completing the act of load conditioning.

EXAMPLE 34

The method of Example 33, further comprising presenting the user with information regarding each of the available sterilization cycles via the touch screen.

EXAMPLE 35

The method of any one or more of Examples 33 through 34, further comprising receiving an indicator data set from a reader of the sterilizing cabinet based on the user's use of the reader to read an identification tag of the biological indicator.

EXAMPLE 36

The method of Example 35, wherein the indicator data set comprises an indicator type, further comprising restricting the plurality of available sterilization cycles based upon the indicator type.

EXAMPLE 37

The method of any one or more of Examples 35 through 36, wherein the indicator data set comprises an indicator expiration date, the method further comprising prompting the user to obtain a new biological indicator when the indicator expiration date indicates that the biological indicator has expired.

EXAMPLE 38

The method of any one or more of Examples 35 through 37, wherein the indicator data set comprises an indicator recall status, the method further comprising prompting the user to obtain a new biological indicator when the indicator recall status indicates that the biological indicator has been recalled by a provider.

EXAMPLE 39

The method of any one or more of Examples 35 through 38, wherein the indicator data set comprises an indicator source, the method further comprising prompting the user to obtain a new biological indicator when the indicator source is not within a set of approved indicator sources.

EXAMPLE 40

The method of any one or more of Examples 33 through 39, further comprising prompting the user via the touch screen display to use a reader of the sterilizing cabinet to read an identification tag of the biological indicator.

EXAMPLE 41

The method of Example 41, further comprising displaying a soft indicator requirement on the touch screen display when: (i) the sterilizing cabinet has not read the identification tag of the biological indicator, and (ii) the sterilizing cabinet has received an indication from the user that the sterilization cycle should begin.

EXAMPLE 42

The method of any one or more of Examples 40 through 42, further comprising displaying a hard indicator requirement on the touch screen display when: (i) the sterilizing cabinet has not read the identification tag of the biological indicator, and (ii) the sterilizing cabinet has received an indication from the user that the sterilization cycle should begin, wherein the hard indicator requirement prevents the sterilization cycle from being performed.

EXAMPLE 43

The method of Example 42, further comprising removing the hard indicator requirement when: (i) the sterilizing cabinet reads the identification tag of the biological indicator, or (ii) the sterilizing cabinet receives a bypass code from the user.

EXAMPLE 44

The method of any one or more of Examples 33 through 43, further comprising displaying via the touch screen display a load placement image, wherein the load placement image comprises: (i) a location for one or more surgical instruments, and (ii) a location for the biological indicator.

EXAMPLE 45

The method of any one or more of Examples 33 through 44, wherein the act of performing load conditioning comprises one or more of: (i) removing moisture from the medical device, and (ii) raising the temperature within the sterilizing chamber.

EXAMPLE 46

The method of any one or more of Examples 33 through 45, further comprising: (a) receiving a set of placement data from a placement sensor of the sterilizing cabinet, wherein the set of placement data indicates the location of the medical device and the biological indicator; and (b) determining whether to perform the sterilization cycle based upon the set of placement data.

EXAMPLE 48

A sterilizing cabinet for sterilizing a medical device comprising a processor, a sterilization chamber, and a touch screen display, wherein the processor is configured to execute instructions to: (a) display a set of sterilization cycles; (b) receive a sterilization cycle selection; (c) display a biological indicator type based upon the sterilization cycle selection, wherein the biological indicator type indicates a biological indicator associated with the sterilization cycle selection; (d) display a set of placement instructions, wherein the set of placement instructions comprises a location for the medical device and a location for a biological indicator; (e) perform a load conditioning process on the medical device in the sterilization chamber; and (f) perform a sterilization cycle on the medical device in the sterilization chamber based upon the sterilization cycle selection.

EXAMPLE 49

The sterilizing cabinet of Example 48, further comprising a reader, wherein the processor is further configured to receive an indicator data set from the reader when a user uses the reader to read an identification tag of the biological indicator.

EXAMPLE 50

The sterilizing cabinet of Example 49, wherein the indicator data set comprises an indicator expiration date, wherein the processor is further configured to execute instructions to display information indicating that the biological indicator has expired when the indicator expiration date indicates that the biological indicator has expired.

EXAMPLE 51

The sterilizing cabinet of any one or more of Examples 49 through 50, wherein the indicator data set comprises an indicator recall status, wherein the processor is further configured to execute instructions to display information indicating that the biological indicator is defective when the indicator recall status indicates that the biological indicator has been recalled by a provider.

EXAMPLE 52

The sterilizing cabinet of any one or more of Examples 49 through 51, wherein the indicator data set comprises an indicator source, wherein the processor is further configured to execute instructions to display information indicating that the biological indicator is incompatible when the indicator source is not within a set of approved indicator sources.

EXAMPLE 53

A sterilizing cabinet comprising: (a) a sterilization chamber; (b) a touch screen display; (c) a biological indicator reader; and (d) a means for guiding a user through the process of selecting a sterilization cycle, selecting a verified biological indicator, placing a medical device in the sterilization chamber, placing the biological indicator in the sterilization chamber, and initiating the sterilization cycle.

VII. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of processing a medical device, the method comprising:
   (a) receiving input from a user selecting a sterilization cycle from a plurality of available sterilization cycles;
   (b) identifying a biological indicator associated with the selected sterilization cycle;
   (c) receiving an indicator data set from a reader of the sterilizing cabinet based on the user's use of the reader to read an identification tag of the biological indicator, wherein the indicator data set comprises verification information for the biological indicator;
   (d) prompting the user via a touch screen display to place the medical device and the biological indicator into a sterilization chamber of a sterilizing cabinet;
   (e) performing load conditioning on the medical device in the sterilization chamber; and
   (f) performing the selected sterilization cycle on the medical device in the sterilization chamber after completing the act of load conditioning.

2. The method of claim 1, further comprising presenting the user with information regarding each of the available sterilization cycles via the touch screen.

3. The method of claim 1, wherein receiving the indicator data set from the reader of the sterilizing cabinet based on the user's use of the reader to read the identification tag of the biological indicator takes place before performing the selected sterilization cycle.

4. The method of claim 3, wherein the verification information from the indicator data set comprises an indicator type, further comprising restricting the plurality of available sterilization cycles based upon the indicator type.

5. The method of claim 3, wherein the verification information from the indicator data set comprises an indicator expiration date, the method further comprising prompting the user to obtain a new biological indicator when the indicator expiration date indicates that the biological indicator has expired.

6. The method of claim 3, wherein the verification information from the indicator data set comprises an indicator recall status, the method further comprising prompting the user to obtain a new biological indicator when the indicator recall status indicates that the biological indicator has been recalled by a provider.

7. The method of claim 3, wherein the verification information from the indicator data set comprises an indicator source, the method further comprising prompting the user to obtain a new biological indicator when the indicator source is not within a set of approved indicator sources.

8. The method of claim 1, further comprising prompting the user via the touch screen display to use the reader of the sterilizing cabinet to read the identification tag of the biological indicator.

9. The method of claim 8, further comprising displaying a soft indicator requirement on the touch screen display when:
   (i) the sterilizing cabinet has not read the identification tag of the biological indicator, and
   (ii) the sterilizing cabinet has received an indication from the user that the sterilization cycle should begin.

10. The method of claim 8, further comprising displaying a hard indicator requirement on the touch screen display when:
    (i) the sterilizing cabinet has not read the identification tag of the biological indicator, and
    (ii) the sterilizing cabinet has received an indication from the user that the sterilization cycle should begin,
    wherein the hard indicator requirement prevents the sterilization cycle from being performed.

11. The method of claim 10, further comprising removing the hard indicator requirement when:
    (i) the sterilizing cabinet reads the identification tag of the biological indicator, or
    (ii) the sterilizing cabinet receives a bypass code from the user.

12. The method of claim 1, further comprising displaying via the touch screen display a load placement image, wherein the load placement image comprises:
    (i) a location for one or more surgical instruments, and
    (ii) a location for the biological indicator.

13. The method of claim 1, wherein the act of performing load conditioning comprises one or more of:
    (i) removing moisture from the medical device, and
    (ii) raising the temperature within the sterilizing chamber.

14. The method of claim 1, further comprising:
    (a) receiving a set of placement data from a placement sensor of the sterilizing cabinet, wherein the set of placement data indicates the location of the medical device and the biological indicator; and
    (b) determining whether to perform the sterilization cycle based upon the set of placement data.

15. A method of processing a medical device, the method comprising:
    (a) displaying a set of sterilization cycles;
    (b) receiving a sterilization cycle selection;
    (c) displaying a biological indicator type based upon the sterilization cycle selection, wherein the biological indicator type indicates a biological indicator associated with the sterilization cycle selection;

(d) displaying a set of placement instructions, wherein the set of placement instructions comprises a location for the medical device and a location for a biological indicator;

(e) performing a load conditioning process on the medical device in a sterilization chamber based upon the sterilization cycle selection;

(f) during the load conditioning process:
  (i) receiving a set of placement data and verifying that the set of placement data indicates that the medical device and the biological indicator have been placed based on the set of placement instructions; and
  (ii) monitoring one or more characteristics of an environment within the sterilization chamber while operating one or more chamber conditioning devices based on the one or more monitored characteristics; and (g) performing a sterilization cycle on the medical device in the sterilization chamber based on the sterilization cycle selection.

16. The method of claim 15, further comprising receiving an indicator data set from a reader configured to read an identification tag of the biological indicator.

17. The method of claim 16, wherein:
(a) the indicator data set comprises a unique identifier;
(b) the method comprises:
  (i) using the unique identifier to determine an indicator recall status for the biological indicator; and
  (ii) displaying information indicating that the biological indicator is defective when the indicator recall status indicates that the biological indicator has been recalled by a provider.

18. A method of processing a medical device, the method comprising:
(a) displaying a set of sterilization cycles;
(b) receiving a sterilization cycle selection;
(c) displaying a biological indicator type based upon the sterilization cycle selection, wherein the biological indicator type indicates a biological indicator associated with the sterilization cycle selection;
(d) displaying a set of placement instructions, wherein the set of placement instructions comprises a location for the medical device and a location for a biological indicator;
(e) performing a load conditioning process on the medical device in a sterilization chamber based upon the sterilization cycle selection;
(f) during the load conditioning process:
  (i) receiving a set of placement data and verifying that the set of placement data indicates that the medical device and the biological indicator have been placed based on the set of placement instructions; and
  (ii) monitoring one or more characteristics of an environment within the sterilization chamber while operating one or more chamber conditioning devices based on the one or more monitored characteristics;
(g) determining whether a unique identifier that identifies the biological indicator has been received and associated with the sterilization cycle selection;
(h) where the unique identifier has not been received, determining a bypass requirement based upon a set of indicator bypass conditions; and
preventing performing a sterilization cycle until the bypass requirement is determined to be satisfied.

19. The method of claim 18, wherein:
(a) the bypass requirement comprises a soft requirement; and
(b) the method comprises:
  (i) displaying a set of instructions for including the biological indicator in the sterilization cycle;
  (ii) displaying a soft bypass button with the set of instructions;
  (iii) determining that the bypass requirement is satisfied based on selection of the soft bypass button; and
  (iv) performing the sterilization cycle on the medical device in the sterilization chamber based on the sterilization cycle selection.

20. The method of claim 18, wherein:
(a) the bypass requirement comprises a hard requirement; and
(b) the method comprises:
  (i) displaying a set of instructions for including the biological indicator in the sterilization cycle;
  (ii) determining that the bypass requirement is satisfied based on receiving the unique identifier, or receiving a passcode and validating the passcode for acceptance; and
  (iii) performing the sterilization cycle on the medical device in the sterilization chamber based on the sterilization cycle selection.

* * * * *